(12) United States Patent
Ollivier

(10) Patent No.: US 10,881,868 B2
(45) Date of Patent: Jan. 5, 2021

(54) TORQUE LIMITING MECHANISM BETWEEN A MEDICAL DEVICE AND ITS IMPLANTATION ACCESSORY

(71) Applicant: SORIN CRM SAS, Clamart (FR)

(72) Inventor: Jean-François Ollivier, Gif sur Yvette (FR)

(73) Assignee: Sorin CRM SAS, Clamart (FR)

( * ) Notice: Subject to any disclaimer, the term of this patent is extended or adjusted under 35 U.S.C. 154(b) by 556 days.

(21) Appl. No.: 15/162,883

(22) Filed: May 24, 2016

(65) Prior Publication Data

US 2017/0340877 A1    Nov. 30, 2017

(51) Int. Cl.
| | |
|---|---|
| *A61N 1/375* | (2006.01) |
| *A61M 25/00* | (2006.01) |
| *A61N 1/372* | (2006.01) |
| *A61N 1/05* | (2006.01) |

(52) U.S. Cl.
CPC ....... *A61N 1/3756* (2013.01); *A61M 25/0082* (2013.01); *A61N 1/372* (2013.01); *A61M 2025/0004* (2013.01); *A61N 1/37518* (2017.08); *A61N 2001/058* (2013.01)

(58) Field of Classification Search
CPC . A61F 2/0063; A61F 2002/0068–0072; A61B 17/0401; A61B 2017/0403–0464; A61N 1/056–0575; A61N 2001/0578–0585
See application file for complete search history.

(56) References Cited

U.S. PATENT DOCUMENTS

| | | | |
|---|---|---|---|
| 6,463,333 B1 | 10/2002 | Ollivier | |
| 8,548,605 B2 | 10/2013 | Ollivier | |
| 8,615,310 B2* | 12/2013 | Khairkhahan | ....... A61N 1/3756 607/122 |
| 2001/0044633 A1 | 11/2001 | Klint | |
| 2002/0065543 A1 | 5/2002 | Gomperz et al. | |
| 2004/0082879 A1 | 4/2004 | Klint | |
| 2005/0085883 A1 | 4/2005 | Ollivier et al. | |
| 2007/0135882 A1 | 6/2007 | Drasler et al. | |
| 2007/0135883 A1 | 6/2007 | Drasler et al. | |
| 2009/0204170 A1 | 8/2009 | Hastings et al. | |

(Continued)

FOREIGN PATENT DOCUMENTS

| | | |
|---|---|---|
| EP | 2 394 695 A1 | 12/2011 |
| EP | 2 394 695 B1 | 9/2012 |

OTHER PUBLICATIONS

Preliminary Search Report for French Patent Application No. 1356020, dated Oct. 22, 2013, 2 pages.

(Continued)

*Primary Examiner* — Gregory A Anderson
(74) *Attorney, Agent, or Firm* — Foley & Lardner LLP

(57) ABSTRACT

A torque limiting mechanism between a medical device and an implantation accessory is disclosed. In a particular embodiment, a delivery system for a leadless active implantable medical device includes a delivery catheter and a torque shaft disposed within the delivery catheter. The delivery system also includes a docking cap having a distal end for engaging an attachment mechanism of the leadless active implantable medical device. The delivery system also includes a torque limiting component coupled to a distal end of the torque shaft and a proximal end of the docking cap.

10 Claims, 14 Drawing Sheets

(56) References Cited

U.S. PATENT DOCUMENTS

| | | | |
|---|---|---|---|
| 2010/0274338 A1* | 10/2010 | Ollivier | A61N 1/0573 607/127 |
| 2011/0301686 A1 | 12/2011 | Bowman et al. | |
| 2011/0307043 A1* | 12/2011 | Ollivier | A61N 1/059 607/127 |
| 2012/0095539 A1 | 4/2012 | Khairkhahan et al. | |
| 2012/0184987 A1 | 7/2012 | Sirota | |
| 2014/0378991 A1* | 12/2014 | Ollivier | A61N 1/0565 606/129 |
| 2014/0378992 A1* | 12/2014 | Ollivier | A61N 1/0573 606/129 |

OTHER PUBLICATIONS

Preliminary Search Report for French Patent Application No. 1356021, dated Oct. 23, 2013, 2 pages.

* cited by examiner

TORQUE LIMITING MECHANISM BETWEEN A MEDICAL DEVICE AND ITS IMPLANTATION ACCESSORY

FIELD OF THE DISCLOSURE

The present disclosure generally relates to active implantable medical devices that monitor heart rhythm and/or deliver electrical pulses to the heart for stimulation, resynchronization and/or defibrillation.

The present disclosure further relates to the implantation of an active implantable medical device provided at the distal end with an anchoring mechanism adapted to penetrate and anchor the device to the tissue of a body wall at a chosen implantation site. Further still, the present disclosure relates to a torque limiter for limiting the torque that can be applied while penetrating and anchoring the device to the tissue at the implantation site.

BACKGROUND

An example of an anchoring member for an implantable medical device includes a projecting helical screw axially extending from the medical device body and adapted to penetrate the heart tissue by a screwing motion at the implantation site. Other anchoring arrangements may include needles, hooks, barbs, etc., for penetrating and anchoring the device to the tissue.

Active implantable medical devices that are in the form of a capsule may be implanted in a heart chamber (ventricle, atrium or even arterial left heart chamber). The device may be referred to as "capsule," "autonomous capsule" or "leadless capsule." The capsule has no physical connection to another implanted device (such as the housing of a stimulation pulse generator) nor to an external device (such as a programmer or monitoring device). Accordingly, the capsule is referred to as a "leadless capsule", to distinguish it from electrodes or sensors located at the distal end of a conventional lead, which is traversed throughout its length with one or more conductors galvanically connecting the electrode or sensor to a generator at an opposite, proximal, end of the lead.

The leadless capsule may be an endocardial capsule (capsule attached to the inner wall of an atrial or ventricular chamber), as opposed to an epicardial capsule fixed to the external wall of the heart. The implantation of the endocardial capsule involves going through the peripheral venous system using an image intensifier to maneuver the capsule to the selected implantation site in a precise and secure manner. Once the site is reached and the capsule is firmly attached in the heart wall, the operator may "release" the capsule, or more particularly, disconnect the capsule from the implantation accessory.

U.S. 2012/0095539 A1, hereby incorporated by reference in its entirety, discloses an implantation accessory for an endocardial electrostimulation leadless capsule. This accessory includes a steerable catheter carrying the capsule. The steerable catheter houses in its inner lumen at its end a wire which is distally connected to the capsule and which is operable in translation and rotation from the proximal end by a handle provided for the practitioner. In a first embodiment, the capsule is mounted to the catheter tip by a system of male/female nesting and the wire end is screwed to the back of the capsule. The retention wire keeps the two elements of the coupling system fitted into each other by a slight tension on the wire, the latter being locked in translation in the manipulation handle. In a second embodiment, the wire remains attached to the capsule after it has been separated from the catheter, so as to act as a safety wire in case it is necessary to reoperate on the capsule after implantation.

U.S. Pat. No. 8,548,605 (Sorin CRM SAS), hereby incorporated by reference in its entirety, discloses another autonomous intracardiac capsule assembly with an implantation accessory. The capsule holds on the sidewall of the tubular body coupling fingers cooperating with a helical guide carried by the distal end of the implantation accessory. The direction of helix of the helical guide is opposite to that of the anchoring screw of the capsule, so as to transmit the screwing torque of the anchoring screw in the heart wall. When the front face of the capsule is brought into contact with the heart wall, the progressive separation of the capsule with the implantation accessory occurs by further screwing of the catheter causing the coupling fingers to slide between the turns of a helical compression spring. The torque limiter effect is thus being obtained by the compression of this helical spring.

Acceptance of endocardial leadless capsules by practitioners may depend on a variety of factors, including: providing a procedure similar to the current practice, which makes use of well-known and mastered practitioners gestures: subclavian or femoral puncture, insertion and manipulation of a catheter via preformed stylets during the approach phase of the selected implantation site, fastening of the screw or barb type, catheter manipulation of the electrophysiology type, etc.; limiting the risk of coring of the tissues due to excessive tightening which may damage the wall or worse, puncture it (especially in the case of implantation into a thin wall as the atrial septum or the apical region the right ventricle); providing a safe and effective way to remove the capsule intraoperatively or postoperatively and/or reposition the capsule, even after release from the delivery system; no risk of migration of the capsule during the acute phase response; certainty of a good fixation of the capsule before removing the implantation accessories; system designed for a femoral approach; no risk of damage by the anchoring member (screw, hook, needle, etc.) throughout the implantation process, including the navigation in the venous network and the approach phase to the selected implantation site; quick procedure, with an implantation target time of approximately 30 minutes "skin-to-skin", comparable to that of the implantation of a generator and a conventional ventricular lead; safe operation, including in the case of: i) improper handling, and ii) premature discontinuation of the procedure; low cost of manufacturing the implantation system.

SUMMARY

A delivery system with a torque limiter may be used to implant a leadless capsule having an anchoring screw at an implantation site, such as a heart wall. The delivery system may be a catheter with a handle at the proximal end and a torque shaft (or sub-catheter) that traverses the entire length of the catheter and transfers radial torque from the handle down to the distal end of the catheter. At the distal end of the catheter, the distal end of the torque shaft couples to the torque limiter. The torque limiter also couples to either a docking feature that receives a leadless capsule, or directly to a proximal end of the leadless capsule. Although not perceptible to the catheter operator, the radial torque required to anchor the leadless capsule is less than the torque required to continue rotation after fully anchoring the leadless capsule, and without the torque limiter, the operator may inadvertently tear, or even puncture the tissue wall, which can be fatal if the tissue wall is a heart wall. The torque limiter limits the radial torque transmitted from the torque shaft to the leadless capsule so that the capsule will no longer rotate after it has been fully anchored to the implantation site, even if the catheter operator continues to rotate the torque shaft.

In a particular embodiment, a delivery system for a leadless active implantable medical device includes a delivery catheter and a torque shaft disposed within the delivery catheter. The delivery system also includes a docking cap having a distal end for engaging an attachment mechanism of the leadless active implantable medical device. The delivery system also includes a torque limiting component coupled to a distal end of the torque shaft and a proximal end of the docking cap.

In another particular embodiment, a torque limiter for a delivery system of a leadless active implantable medical device includes a first interface for coupling to a docking feature of the delivery system where the docking feature secures in rotation the leadless active implantable medical device. The torque limiter also includes a second interface for coupling to a distal end of a torque shaft of a delivery system. The torque limiter limits the torque transmission from the torque shaft to the docking feature when radial torque is applied to the torque shaft.

In another particular embodiment, a delivery system for a leadless active implantable medical device includes an outer catheter and an inner catheter disposed within the outer catheter. The delivery system also includes an interface having a distal end for engaging an attachment mechanism of the leadless active implantable medical device. The delivery system also includes a torque limiting feature coupled to a distal end of the inner catheter and a proximal end of the interface.

Other aspects, advantages, and features of the present disclosure will become apparent after review of the entire application, including the following sections: Brief Description of the Drawings, Detailed Description, and the Claims.

DETAILED DESCRIPTION

Figure 1A:
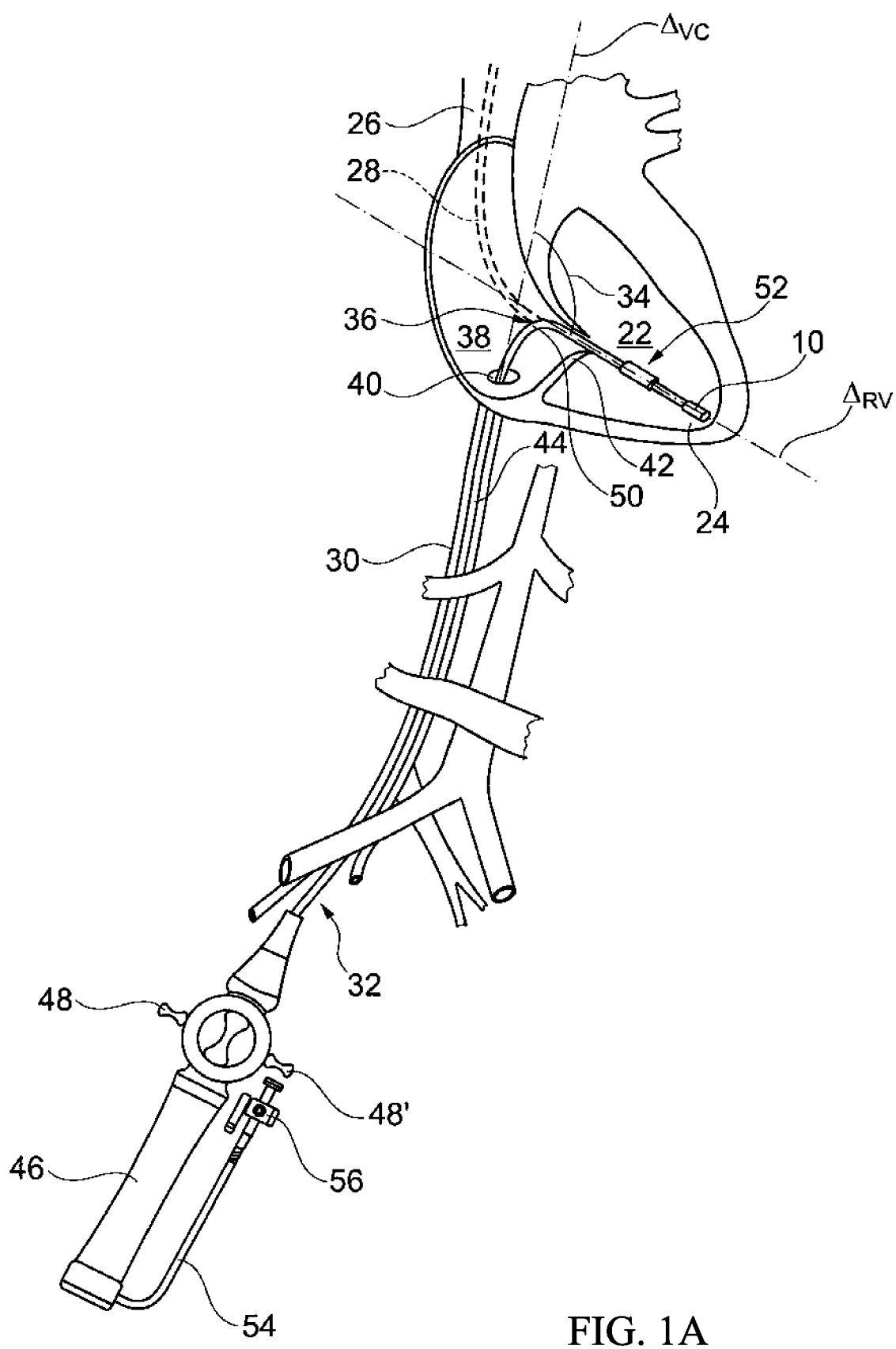
FIG. 1A illustrates the implantation accessory or delivery system and the capsule, in position, with a schematic representation of the femoral approach and of the chambers of the heart.

A torque limiting mechanism may be provided between an implantation accessory and a medical device (corresponding, respectively, to the sub-catheter and to the leadless capsule in the previous particular case). The torque limiting mechanism may include an elastic deformable component used in radial compression (e.g., for its pinch effect). The elastic component may be a coil spring, and can play both the role of a releasable connection and of torque limiter against excessive tightening action which could result in a coring of the tissues.

In some embodiments, the first disconnectable fastening mechanism includes a deformable elastic component, such as a helical spring which cooperates with a rigid object, such as a central core on the capsule. The spring extends around the core such that it exerts on the latter a radial constriction effect, the spring and the core being configured to be disengaged under the effect of a torque applied to the spring at one end thereof, having the effect to reduce said radial constriction to release the core.

In some embodiments, the proximal end of the spring is secured to the distal end of the sub-catheter and the distal end of the spring is free. The core may be an axial lashing rod carried by the proximal end of the capsule and secured in rotation with the latter.

When the capsule includes an anchoring screw, the direction of the coil spring may be the same as that of the anchoring screw. The value of the torque applied to the spring that is effective to reduce said radial constriction to release of the core is determined. This torque value depends on the geometry of the spring and the elasticity of the material which constitutes it, so as to be lower than a predetermined limit corresponding to a torque of the anchoring screw in the tissue of the implantation site, without coring of this tissue.

According to an exemplary embodiment, a medical device may include, at its distal end, an anchoring member capable penetrating a tissue wall of a body, and an in situ implantation accessory of the medical device. The implantation accessory may include a deformable elongate tubular member having a disconnectable mechanism for support of the medical device and guiding of the medical device to a site of implantation. The disconnectable mechanism includes a helical spring that cooperates a central core and is suitable for securing in translational and in mutual rotation the tubular element of the implantation accessory and the medical device, and able to decouple the medical device with the tubular member of the implantation accessory under the effect of a rotation applied to the tubular member from the proximal end thereof.

Typically, the spring extends around the core such that it exerts on the latter a radial constriction effect, the spring and the core being capable of disengagement under the effect of a combined torque and traction applied to the spring at one end thereof, being effective to reduce said radial constriction to release the core.

The proximal end of the spring may be secured to the distal end of the tubular member of the implantation accessory, the distal end of the spring is free, and the core is an axial lashing rod carried by a proximal end of the medical device and secured in rotation to the latter.

When the medical device bears an anchoring screw, the direction of the coil spring may be the same as that of the anchoring screw. The value of said torque applied to the spring that is effective to reduce said radial constriction to release the core is determined. The torque value depends on the geometry of the spring and the elasticity of the material which constitutes it, so as to be always lower to a predetermined limit value, corresponding to a holding torque limit of the anchoring screw in the tissue of the implantation site, without coring of this tissue. Finally, the distal end of the spring is advantageously a rounded end.

A method for implanting a medical device includes introducing a medical device provided at its distal end with an anchoring member adapted to penetrate tissue of a wall of a cavity of a heart at a target location in a cavity of the heart, wherein a proximal end of the medical device is coupled to a distal end of an elongated tubular element with a fastening mechanism. The fastening mechanism comprises an elastic deformable component cooperating with a rigid component. The method further includes rotating the elongated tubular element to cause rotation of the medical device and engage the anchoring member with the tissue of the cavity of the heart to implant the anchoring member into the tissue. After implantation, rotation of the elongated tubular element is continued in the same direction so as to generate an excess torque to thereby release the fastening mechanism and decouple the elongated tubular member from the medical device.

Referring to FIG. 1A, a schematic representation of the femoral access route and the chambers of the heart are show as well as an implantation accessory, or delivery system, for an autonomous capsule of the leadless type 10. Various implementations of the embodiment shown in FIG. 1A and/or other embodiments described in the present disclosure may utilize features similar to those discussed in U.S. patent application Ser. No. 14/312,410 and U.S. patent application Ser. No. 14/312,381, the disclosures of which are incorporated herein by reference in their entireties.

The leadless capsule 10 may be implanted in the right ventricle 22, including at the bottom of the ventricle in the region of the apex 24. A conventional stimulation lead (connected to a remote generator) would typically be implanted via the subclavian vein 26, as illustrated by dashed lines 28, so that the end of the lead would be approximately oriented in the ARV axis of the right ventricle and thus could easily pass through the tricuspid valve and reach the apex 24 of the right ventricle 22. However, this implantation approach may not be feasible for implantation of some leadless capsules.

The leadless capsule 10 may be implanted via the vena cava 30, from a femoral puncture 32. The axis of approach, ΔVC, of the vena cava has a strong angulation (angle 34) with the axis ΔRV of the right ventricle. The implantation accessory may form a curvature 36 at the right atrium 38 in order to pass from the sinus 40 of the vena cava to the tricuspid valve 42 to then reach the cavity of the right ventricle 22. Similar difficulties arise for implantation into the left ventricle, the implantation access then involving an arterial femoral puncture and the passage of the aortic arch.

Such a maneuver may be performed using a "steerable" catheter with a catheter tube 44 handled from the proximal end by an operating handle 46. Using the handles 48, 48' the physician can create and adjust a curvature 50 to guide the distal end 52 of catheter 44 accurately, typically with an orientation up to 180° in both directions with a variable radius of curvature, of the order of 5 to 60 cm. The handle 46 may also be provided with a purge drain lateral track 54 and a valve 56.

Figure 1B:
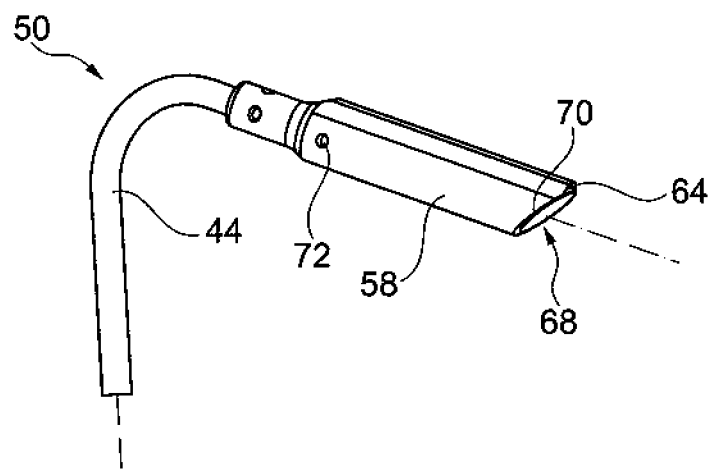
FIG. 1B shows the distal end of a remotely steerable catheter provided with its protection tip, in the retracted position of the leadless capsule.

Referring to FIG. 1B, the distal end of the steerable catheter 44 is provided with a tubular protection tip 58 having a central recess 60 (see FIG. 3A) for housing the capsule 10 in a "retracted position". The tip 58 protects the capsule 10, including the anchoring screw 14, and the tissue from the anchoring screw 14 during the intravenous passage of curves, angulations, valves, etc.

The outer diameter of the steerable catheter 44 may be between 10 and 15 French (6.6 to 10 mm) and have an inner lumen diameter of between 8 and 12 French (2.66 mm to 4 mm). The tubular tip 58 is sized to house the capsule 10 and may have an inside diameter of about 21 French (7 mm) depending on the diameter to the leadless capsule 10. Furthermore, the catheter may include a coiled guidewire previously introduced into the vasculature.

Figure 2A:
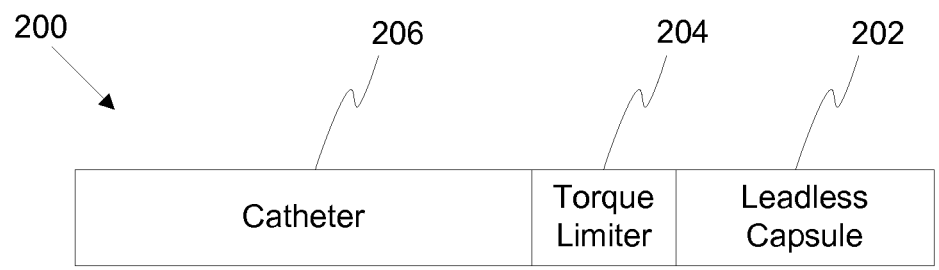
FIG. 2A is a block diagram of a particular illustrative embodiment of a leadless capsule delivery system with a torque limiter.

Referring to FIG. 2A, a particular illustrative embodiment of a delivery system (also referred to as an implantation accessory) is disclosed and generally designated 200. The delivery system 200 delivers a leadless capsule 202 to an implantation site, and includes a torque limiter 204 and a catheter 206. The leadless capsule 202 may include a helical anchoring screw for penetrating and anchoring to a tissue wall within the body, such as a heart wall. A distal end of the catheter 206 is coupled to the torque limiter 204. A sub component of the catheter 206 may couple the catheter 206 to the torque limiter 204. The sub component of the catheter 206 may be referred to as a sub-catheter, an inner catheter (where the catheter 206 is an outer catheter), or a torque shaft. The torque limiter 204 is also coupled to the leadless capsule 202.

In some embodiments, the torque limiter 204 may be permanently affixed to the catheter 206 (e.g., the sub-catheter, inner catheter, or torque shaft), and the torque limiter 204 may couple to the proximal end of the leadless capsule 202 via an interference fit or a friction fit. In some embodiments, the torque limiter 204 may be permanently affixed to the proximal end of the leadless capsule 202, and the torque limiter 204 may be coupled to the catheter 206 via an interference fit or a friction fit. Regardless of the coupling, the torque limiter 204 limits the radial torque transmitted to from the proximal end of the catheter 206 (e.g., a handle of the catheter 206) to the leadless capsule 202 in at least a first radial direction corresponding to the radial direction for screwing the leadless capsule 202 into the tissue wall.

For example, when the proximal end of the catheter 206 is turned in first radial direction to screw the leadless capsule 202 into a tissue wall at the implantation site, the radial torque transmitted from the catheter 206 and through the torque limiter 204 is sufficient to rotate the leadless capsule 202 and drive the anchoring screw into the tissue wall until a distal face of the leadless capsule 202 contacts the tissue wall. When the face of the leadless capsule 202 contacts the tissue wall, the radial torque required to continue to rotate the capsule increases to a value T1. However, the torque limiter 204 provides a torque limit such that the radial torque transmitted from the handle of the catheter 206 to the leadless capsule 202 never reaches T1. In some embodiments, the torque is not limited in a second radial direction for unscrewing the leadless capsule 202 from the tissue wall. In some embodiments, the torque limit in the second radial direction is the same as the torque limit in the first radial direction. In some embodiments, the torque limit in the second radial direction is greater than the torque limit in the first direction.

The torque limiter 204 may include an interface for coupling to the catheter 206 (e.g., where the interface is the portion of the torque limiter 204 that couples to the catheter 206) and an interface for coupling to the leadless capsule 202 (e.g., where the interface is the portion of the torque limiter 204 that couples to the leadless capsule 202). One or both of the interfaces may be an inner surface of a socket that receives a key (e.g., key may be a sub-catheter or shaft of a leadless capsule), an outer surface of a cylinder that fits into a socket (e.g., the socket may be an inner surface of a hollow catheter, or inner surface of a hollow shaft of a leadless capsule), a deformable elastic planar sheet (see FIGS. 9A-D) within a socket to provide tension when the key is inserted, an inner or outer surface of turns of a helical spring or coil, a clip, a latch, a surface of a layer of material (e.g., a coating, fabric, or sleeve), or any other elastic deformation of the torque limiter 204 or component of the torque limiter 204 able to generate a controlled friction when interacting with another component (e.g., the catheter 206 or leadless capsule 202). The interfaces may also include one or more features to facilitate permanent attachment such as holes or gaps.

The torque limiter 204 may also comprise a fabric, coating, sleeve, or some other material in a layer form disposed between the catheter 206 and leadless capsule 202 in a socket and key configuration where the catheter 206 and leadless capsule 202 form the socket and key in no particular order.

Figure 2B:
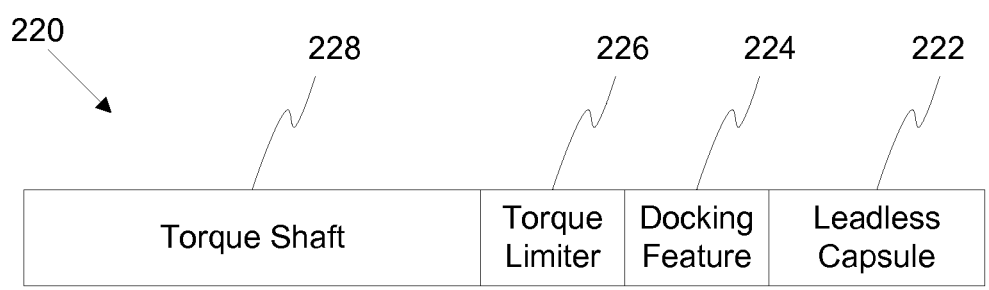
FIG. 2B is a block diagram of a particular illustrative embodiment of a leadless capsule delivery system with a torque limiter and docking feature.

Referring to FIG. 2B, a particular illustrative embodiment of a delivery system (also referred to as an implantation accessory) is disclosed and generally designated 220. The delivery system 220 delivers a leadless capsule 222 to an implantation site, and includes a docking feature 224, a torque limiter 226, and a torque shaft 228. The distal end of the leadless capsule 222 may include a helical anchoring screw for penetrating and anchoring to a tissue wall within the body, such as a heart wall. The torque shaft 228 may be a sub component of, and disposed within, a delivery catheter. The torque shaft 228 may be used to transmit radial torque from a catheter handle to the distal end of the delivery catheter. A distal end of the torque shaft 228 is coupled to the torque limiter 226. The torque limiter 226 may also be coupled to the docking feature 224. The docking feature 224 may be secured in translation with the torque shaft 228. The docking feature 224 receives and couples to the proximal end of the leadless capsule 222. The docking feature 224 carries the leadless capsule 222 to the implantation site and may be secured in rotation with the leadless capsule 222 such that the docking feature 224 transmits radial torque received from the torque limiter 226 to the leadless capsule 222.

In some embodiments, the torque limiter 226 may be permanently affixed to distal end of the torque shaft 228, and the torque limiter 226 may couple to the docking feature 224 via an interference fit or a friction fit. In some embodiments, the torque limiter 226 may be permanently affixed to the docking feature 224, and the torque limiter 226 may be coupled to the distal end of the torque shaft 228 via an interference fit or a friction fit. In some embodiments, the torque limiter 226 may be coupled to distal end of the torque shaft 228 and the docking feature via respective interference fits. Regardless of the coupling, the torque limiter 226 limits the radial torque transmitted to from the proximal end of the torque shaft 228 (e.g., a handle of the catheter) to the docking feature 224, and thus the leadless capsule 222, in at least a first radial direction corresponding to the radial direction for screwing the leadless capsule 222 into the tissue wall.

For example, when the proximal end of the torque shaft 228 is turned in first radial direction (e.g., the direction to screw the leadless capsule 222 into a tissue wall at the implantation site), radial torque transmitted from the torque shaft 228 to the docking feature 224 through the torque limiter 226 is sufficient to rotate the leadless capsule 222 and drive the anchoring screw into the tissue wall until a distal face of the leadless capsule 222 contacts the tissue wall. When the face of the leadless capsule 222 contacts the tissue wall, the radial torque required to continue to rotate the capsule increases to a value T1. However, the torque limiter 226 provides a torque limit such that the radial torque transmitted from the torque shaft 228 to docking feature 224, and thus the leadless capsule 222, never reaches T1. Therefore, the leadless capsule 222 and the corresponding anchoring screw no longer rotate in the first radial direction even with continued rotation of the torque shaft 228. This avoids unwanted tearing of the tissue at the implantation site. In some embodiments, the torque is not limited in a second radial direction for unscrewing the leadless capsule 222 from the tissue wall. In some embodiments, the torque limit in the second radial direction is the same as the torque limit in the first radial direction. In some embodiments, the torque limit in the second radial direction is greater than the torque limit in the first direction.

In some embodiments, the docking feature 224 may be a docking cap similar to the docking cap described in U.S. Pat. No. 8,615,310, which is hereby incorporated by reference in its entirety. For example, the docking feature may provide a socket or a cavity that is shaped to receive a proximal end of a leadless capsule. In some embodiments, the docking feature 224 may provide a docking key that is designed to fit into a socket provided at the proximal end of a leadless capsule. The docking feature 224 may couple to the leadless capsule in a variety of other ways, for example, the docking feature may use one or more of a clip, a latch, a snap, corresponding threads, and so on. Regardless of the mechanism used to couple the leadless capsule 222 to the docking feature 224, the purpose of the docking feature 224 is to secure the leadless capsule 222 so that the leadless capsule 222 may be routed by the delivery system 220 to the implantation site, and to secure the leadless capsule 222 in rotation so that the anchoring screw of the leadless capsule 222 may be screwed into the tissue at the implantation site.

The torque limiter 226 may include a first interface for coupling to the torque shaft 228 (e.g., where the first interface is the portion of the torque limiter 226 that coupled to the torque shaft 228) and a second interface for coupling to the leadless capsule 222 (e.g., where the interface is the portion of the torque limiter 226 that couples to the leadless capsule 222). One or both of the interfaces may be an inner surface of a socket that receives a key (e.g., the key may be the torque shaft 228 or docking shaft of a docking feature 224), an outer surface of a cylinder that fits into a socket (e.g., the socket may be the inner surface of a hollow torque shaft 228, or inner surface of a hollow shaft of the docking feature 224), a deformable elastic planar sheet (see FIGS. 9A-D) within a socket to provide tension when the key is inserted, an inner or outer surface of turns of a helical spring or coil, a clip, a latch, a surface of a layer of material (e.g., a coating, fabric, or sleeve), or any other elastic deformation of the torque limiter 226 or component of the torque limiter 226 able to generate a controlled friction when interacting with another component (e.g., the torque shaft 228 or leadless capsule 222). The interfaces may also include one or more features to facilitate permanent attachment such as holes or gaps.

Figure 3A:
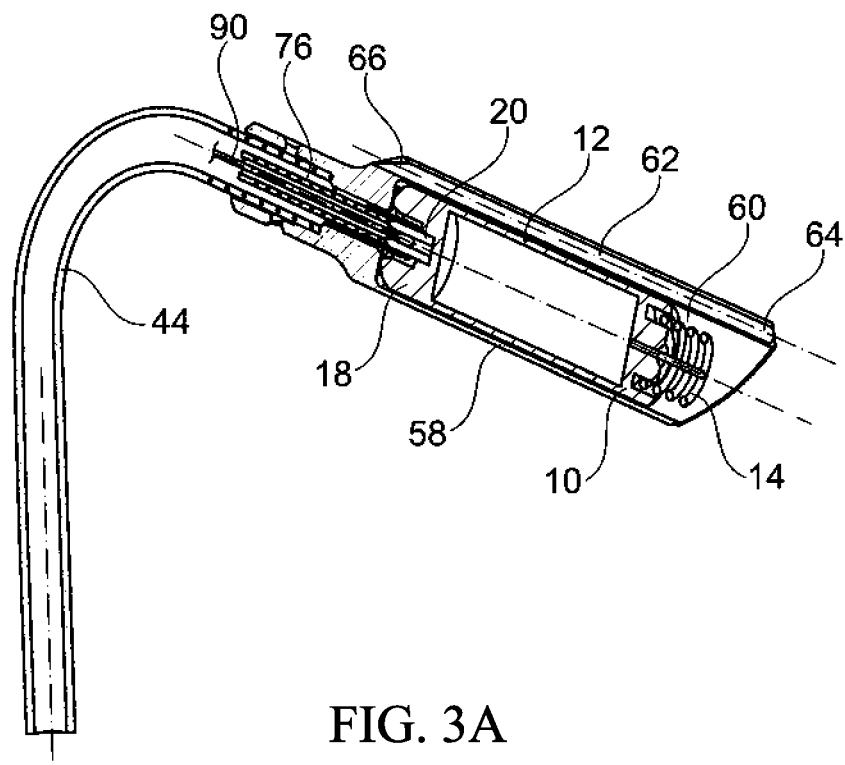
FIG. 3A is an enlarged, sectional view of FIG. 1B, showing the general configuration of the various internal elements and the leadless capsule housed inside the protection tip.
Figure 10:
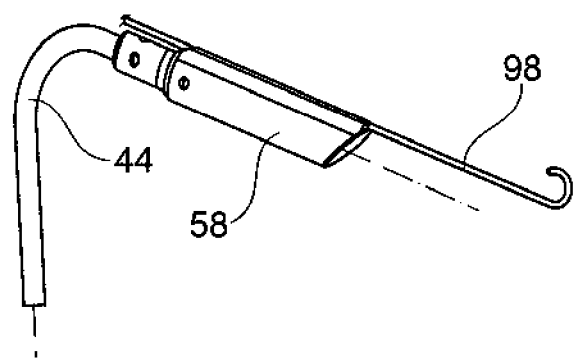
FIG. 10 shows the distal end of the remotely steerable catheter provided with its protection tip mounted on a coiled guidewire used to advance this tip from the femoral puncture until the selected implantation site.
Figure 11:
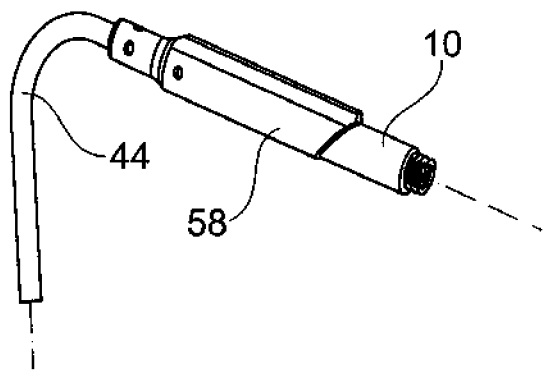
FIG. 11 shows the distal end of the remotely steerable catheter provided with its protection tip, with the leadless capsule partially emerged of this tip.

Referring to FIG. 3A, to accommodate the guidewire, the tubular tip may be provided with an eccentric lateral lumen 62 extending axially the length of the tip and opening at the distal 64 and proximal 66 sides, preferably extending over the entire length of the tip 58. The inner diameter of the lateral lumen 62 allows for the introduction of a conventional coiled guidewire of a diameter of, for example, 3 French (1 mm), and the sliding of the tip, and therefore of the entire steerable catheter 44, through the vasculature (this configuration is notably shown in FIG. 10, wherein the reference 98 designates the coiled guidewire). Alternatively, the eccentric lateral lumen 62 may be extended along the body of the steerable catheter 44 to facilitate the pushing of the coiled guidewire and prevent any curling phenomenon thereof.

The eccentricity of the lumen 62 combined with the beveled profile of the tip allows easy progression into the venous system by a "sidewire" technique. In addition, the front panel 68 (see FIG. 1B), the most distal area of the tip 58, may be shaped to have a minimum front bearing surface to avoid any risk of perforation.

Referring to FIG. 1B, a radiopaque marker 70 may be provided in front of the tubular tip 58 on the most distal surface of this tip, to more efficiently identify the capsule outlet. Finally, one or more drain holes 72 may be disposed proximal to the tip to prevent piston effect upon injection of contrast medium, which might otherwise result in pushing the capsule 10 out of the protection tip 58.

Figure 3B:
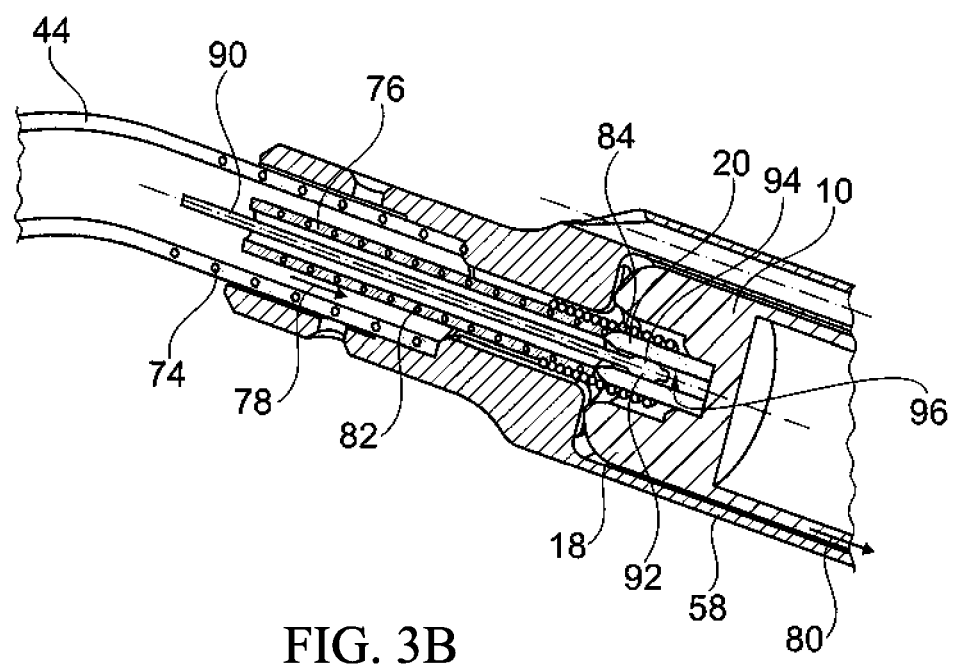
FIG. 3B is an enlarged view of the sectional view of FIG. 3A, in the region of the connection with the proximal end of the leadless capsule.

Referring to FIG. 3B, the catheter 44 may be formed with a reinforced structure 74, such as a wire mesh or a coil embedded in the thickness of the catheter wall, so as to provide a torque transmission capability from torque exerted at the handle to the distal end of the catheter.

The implantation accessory may further include a sub-catheter 76 (also referred to herein as a torque shaft), introduced into the central lumen of the steerable catheter 44, and movable in rotation and in translation relative to the catheter 44. In some embodiments, the sub-catheter 76 ensures the deployment of the capsule 10 out of the protection tip and advances the capsule to the implant site by a translation movement over a sufficient length, typically from to 2 to 6 cm depending on the anatomy of the patient. Arrow 78 indicates the translation of the sub-catheter 76 within the steerable catheter 44, and arrow 80 indicates the translation of the capsule 10 out of the protection tip 58. The sub-catheter 76, or torque shaft, is provided with a reinforced structure to transmit torque from the proximal end (at the operating handle) to its distal end.

The sub-catheter 76 may be a conventional guide catheter sized from 4 to 6 French (1.33 to 2 mm). The sub-catheter 76 may have a proximal "Luer-Lok" connection for the rapid mounting of a multifunction adapter such as a rotational hemostasis valve or other adapter compatible with this sealed connection standard. Furthermore, the sub-catheter 76 may be used to inject a contrast to the back of the capsule 10 so as to accurately monitor the operation under fluoroscopy.

In some embodiments, a fastening mechanism may be provided to couple an implantation accessory or delivery system (such as a catheter) with an autonomous leadless capsule or a probe head of a pacing lead. The leadless capsule or pacing lead may be provided at its distal end with an anchoring mechanism adapted to penetrate and anchor to a body tissue, such as a cardiac wall. The fastening mechanism may employ an elastic deformable component, such as helical spring 84, which may be used for its radial compression properties, that is to say for the pinch or throttle effect a spring can exert around a rigid component, such as a core inserted into the helical form. In other embodiments, the elastic deformable component may be a lamella that provides radial compression about the core.

The geometry and elasticity of the material of the elastic deformable component are chosen to produce an interference fit caused by the radial compression (the pinch effect) between the elastic deformable component and a core. Referring to FIG. 3B, the core may be a lashing rod 20, or shaft, with a rounded end located axially on the proximal portion 18 of the capsule 10 and outwardly oriented. This lashing rod 20 may be shaped to optimize the disengagement function.

Figure 4A:
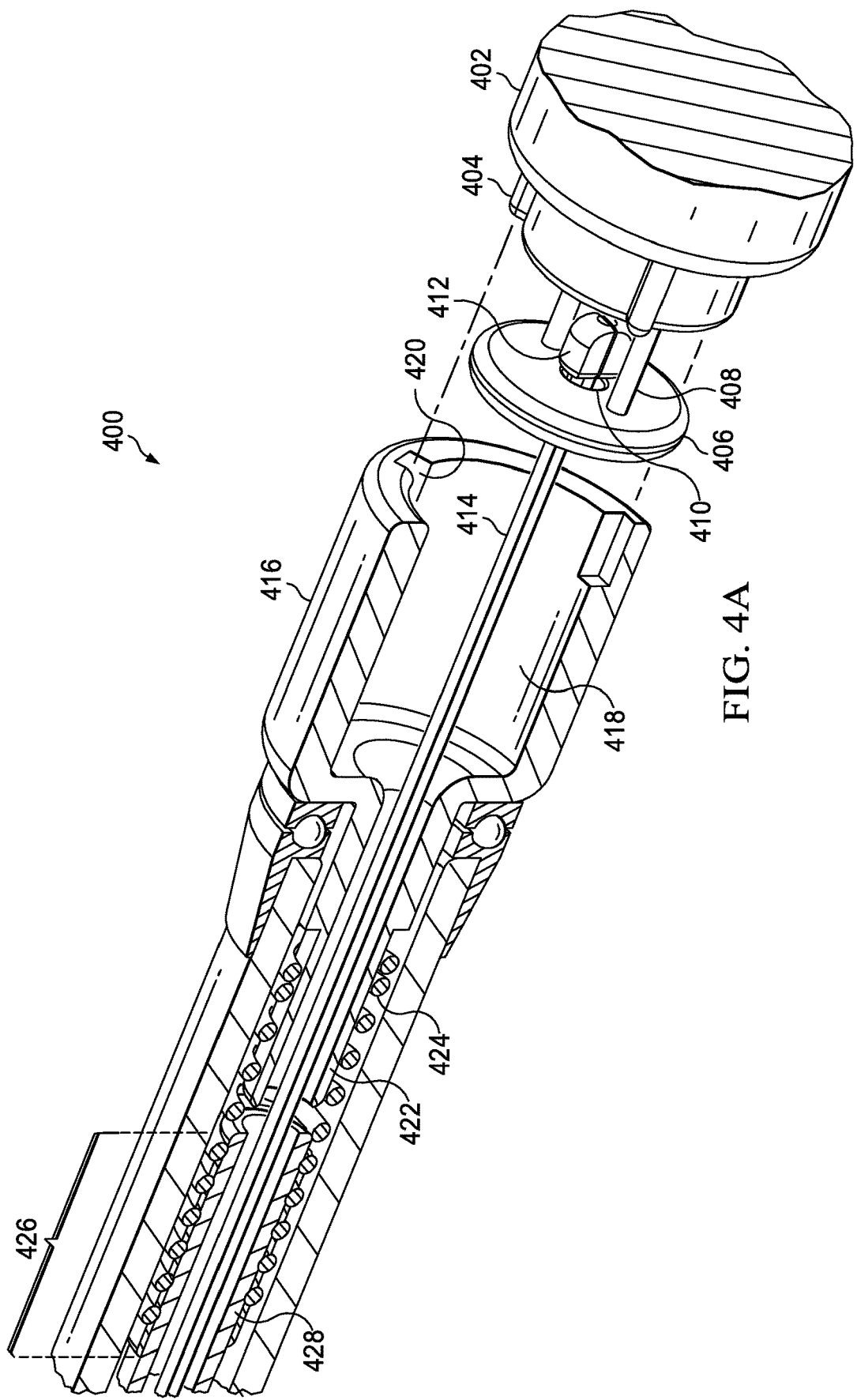
FIG. 4A is a sectional view of a particular illustrative embodiment showing the general configuration of the various internal elements of the leadless capsule delivery system with a docking feature.

Referring to FIG. 4A, a particular illustrative embodiment of a delivery system (also referred to as an implantation accessory) is disclosed and generally designated 400. The delivery system 400 delivers a leadless capsule 402 to an implantation site. The leadless capsule may be similar to the leadless capsule described in U.S. Pat. No. 8,615,310 which has already been incorporated by reference in its entirety. The leadless capsule 402 may include a helical anchoring screw at its distal end for anchoring to a tissue wall of the body, such as a heart wall. At a proximal end, the leadless capsule 402 may include one or more torque keys 404, an attachment feature 406 secured to the leadless capsule 402 by two or more attachment members 408, and a hole 410 in the attachment feature 406. The delivery system 400 may further include one or more distal features 412 coupled to the distal end of one or more tethers 414, a docking cap 416 having a cavity 418 shaped to receive the proximal end of the leadless capsule 402 including the attachment feature 406. The wall of the cavity 418 may include one or more torque slots 420 corresponding to the one or more torque keys 404 of the leadless capsule 402. The docking cap 416 further includes a docking shaft 422 to which a torque limiter, such as helical spring 424, may be coupled via an interference fit or friction fit (e.g., radial compression or constriction of the helical spring 424 around the docking shaft 422). The delivery system 400 further includes a torque shaft 428 coupled at its distal end to the torque limiter (e.g., the helical spring 424). The coupling between the torque shaft 428 and the torque limiter (e.g., the helical spring 424) may be a permanent coupling 426 (e.g., welding or gluing).

The tethers 414 may run the entire length of the torque shaft 428 and may be accessible at a handle at the proximal end of the delivery system 400. The distal features 412 have a cross sectional diameter larger than the cross sectional diameter of the tethers 414. The distal features 412 can be advanced one at a time through the hole 410 in the attachment feature 406. The diameter of each individual distal feature 412 is less than the diameter of the hole 410, however, when the distal features 412 are placed side by side after passing through the hole 410, the combined diameter is greater than the hole 410, which locks the tethers 414 to the leadless capsule 402. The tethers 412 may be retracted so that the proximal end of the leadless capsule 402, including the attachment feature 406, is brought into the docking cap 416 and secured in translation with the docking cap 416. Inside the docking cap, the torque keys 404 are aligned with the torque slots 420 to secure the leadless capsule 402 in rotation with the docking cap 416.

With the leadless capsule 402 properly secured in translation and rotation with the docking cap 416, the delivery system 400 may be used to maneuver the leadless capsule to the implantation site. At the implantation site, the anchoring screw at the distal end of the leadless capsule 402 is brought into contact with a tissue wall and a radial torque in a first radial direction (e.g., the direction to screw the leadless capsule 402 into a tissue wall at the implantation site) is applied at the proximal end of the torque shaft 428. The entire torque shaft 428 rotates in the first radial direction and delivers a radial torque to the helical spring 424 affixed at the distal end of the torque shaft 428. The helical spring 424 transfers the radial torque to the docking cap 416, and thus, the leadless capsule 402, which is locked in rotation with the docking cap 416, causing the leadless capsule 402 to rotate. The rotation of the leadless capsule 402 drives the anchoring screw into the tissue wall at the implantation site. The torque transferred by the helical spring 424 is sufficient to rotate the docking cap 416 and the leadless capsule 402 until the helical screw is driven into the tissue wall far enough so that the distal face of the leadless capsule 402 comes into contact with the tissue wall. The radial torque required to continue to rotate the leadless capsule 402 increases to a value T1. The continued rotation of the leadless capsule 402 could tear the tissue and potentially puncture the tissue wall. If the tissue wall is a heart wall, the puncture could cause cardiac tamponade.

The torque limiter, such as the helical spring 424, provides a limit to the radial torque that may be transferred from the distal end of the torque shaft 428 to the docking cap 416 and the leadless capsule 402. The limit is a value lower than the radial torque value T1 required to continue rotation of the leadless capsule 402. For example, as the radial torque required to rotate the leadless capsule 402 increases, the friction between the torque limiter (e.g., the inner surface of the turns of the helical spring 424) and the outer surface of the docking shaft 422 that forms the interference fit is no longer sufficient to secure the torque limiter (e.g., the helical spring 424) and the docking shaft 422 in rotation. The torque limiter (e.g., the helical spring 424) begins to slide around the docking shaft 422 thereby limiting the radial torque transferred to the docking cap 416, and thus, the leadless capsule 402. Therefore, when the distal face of the leadless capsule 402 contacts the tissue wall, the torque shaft 428 may continue to rotate in the first direction, but the leadless capsule 402 will no longer rotate and cause tearing of the tissue at the implantation site.

The helical spring 424 may be used for its radial compression (radial constriction) properties when interacting with a rigid component, such as the docking shaft 422. For example, when the docking shaft 422 is inserted into the helical spring 424 such that the turns of the spring surround the docking shaft 422, the helical spring 424 exerts a radial compression or constriction on the docking shaft 422 to form an interference fit or friction fit. When the helical spring 424 is rotated in a first radial direction (e.g., the direction to screw the leadless capsule 402 into the tissue wall) the helical spring 424 may exhibit a throttle effect, especially when the torque increases (e.g., when the distal face of the capsule contacts the tissue wall), such that the constriction effect between the turns of the helical spring and the docking shaft 422 decreases. The decrease in constriction, and therefore, friction, causes the helical spring 424 to slide around the docking shaft 422, thereby limiting the torque transmitted to the docking shaft 422 and the leadless capsule 402. When the helical spring 424 is rotated in a second radial direction (e.g., the direction to unscrew the leadless capsule 402), the helical spring 424 exhibits a pinch effect in which the coils constrict or tighten around the docking shaft 422. The pinching effect allows transfer of maximum torque to the docking cap 416 for unscrewing the leadless capsule 402 so that the leadless capsule may be safely removed.

Figure 4B:
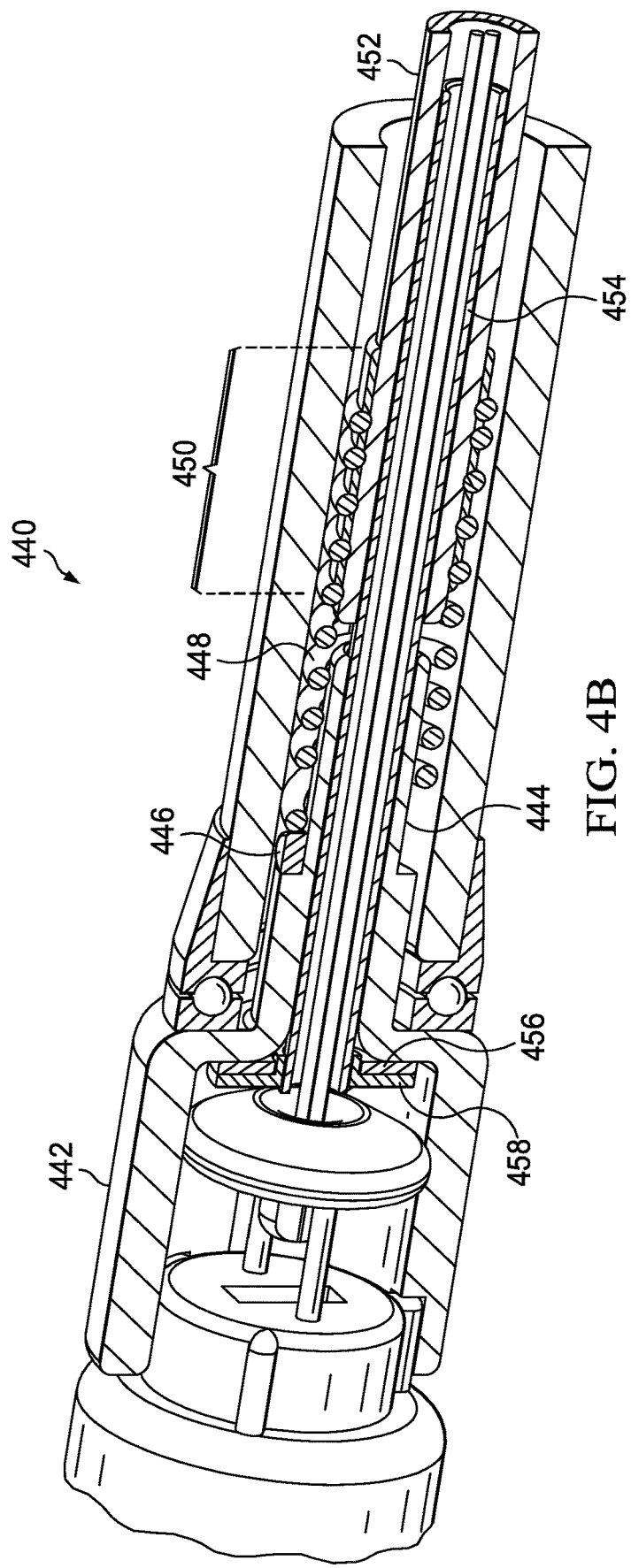
FIG. 4B is a sectional view of a particular illustrative embodiment showing the general configuration of the various internal elements of the leadless capsule delivery system with a docking feature and a projection finger.

Referring to FIG. 4B, a particular illustrative embodiment of a delivery system (also referred to as an implantation accessory) is disclosed and generally designated 440. The delivery system 440 includes a docking cap 442 having a docking shaft 444 with a projection finger 446. The docking cap 442 may be secured in translation with the torque shaft 452. A helical spring 448 may be coupled to a distal end of a torque shaft 452 via a permanent coupling 450, such as by welding or gluing. The helical spring 448 may be axially pre-compressed between the permanent coupling 450 on distal end of the torque shaft 452 and back face of the docking cap 442 at the distal end of the docking shaft 444. The projection finger 446 also interacts with the distal end of the pre-compressed helical spring 448.

To support the pre-compression, a support tube 454 may be provided within the torque shaft 452. The outer surface of the support tube 454 may be glued, welded, or otherwise affixed to the inner surface of the torque shaft 452. The support tube 454 may extend out of the distal end of the torque shaft 452 and into the docking shaft 444. The docking shaft 444 is not affixed to the support tube 454 and may rotate freely around the support tube 454. The support tube may further extend into a proximal end of a cavity of the docking cap 442. At the proximal end of the cavity of the docking cap 442, the support tube 454 may be coupled to one or more plates, such as a first plate 456 and a second plate 458. The first plate 456 may be disposed between a back wall at the proximal end of the cavity and the second plate 458. In some embodiments, the second plate 458 may be permanently affixed to the support tube 454 and the first plate 456 may be either permanently affixed to the back wall of the cavity, permanently affixed to a proximal surface of the second plate 458, or simply pressed between the back wall of the cavity and the proximal surface of the second plate 458. In some embodiments, the first plate 456 may be permanently affixed to the support tube 454 and the second plate 458 may be permanently affixed to a distal side of the first plate 456. In some embodiments, the first plate 456 and the second plate 458 may both be permanently affixed to the support tube 454. The permanent affixation or coupling may be provided by welding (e.g., laser welding), gluing, or otherwise. The first plate 456 may be made from a low friction material, such as Teflon, to limit the friction between the cavity of the docking cap 442 and the second plate 458 (and corresponding support tube 454 to which the second plate 458 is attached). The second plate 458 may be made from a metal, polymer, or other suitable material for use in an implantation accessory. The second plate 458 acts as a stopper to lock, or secure, the docking cap 442 in translation with the torque shaft 452 so that the docking cap 442 will not detach during the implantation procedure.

When the helical spring 448 is rotated by the torque shaft 452 in a first radial direction (e.g., the direction to screw the leadless capsule into a tissue wall), the friction between the distal end of the helical spring 448 and the back face of the docking cap 442 is sufficient to transfer the radial torque required to rotate the docking cap 442 and the leadless capsule to screw the leadless capsule into the tissue wall. However, when the distal face of the leadless capsule contacts the tissue wall, the radial torque required to rotate the capsule increases. The friction between the distal end of the helical spring 448 and the back face of the docking cap 442 is not sufficient to transmit the radial torque required to the docking cap 442. As a result, the spring begins to slide around the docking shaft 444. The distal end of the helical spring 448 slides around the docking shaft 444 until it engages the projection finger 446. The interaction of the helical spring 448 and the projection finger 446 increases the axial compression of the helical spring 448 and the friction between the distal end of the helical spring 448 and the back face of the docking cap 442, which increases the value of the radial torque that may be transmitted to the docking cap 442. However, the value is still not sufficient to transmit the radial torque required to the docking cap 442 when the distal face of the leadless capsule contacts the tissue wall. Therefore, the distal end of the helical spring 448 slides over and past the projection finger 446 and continues to slide around the docking shaft 444. FIGS. 5A-5D and the corresponding descriptions further illustrate and describe the interaction of the helical spring and the projection finger.

When the helical spring 448 is rotated by the torque shaft 452 in a second direction (e.g., the direction to unscrew the leadless capsule), radial torque is transmitted to the docking cap 442. If the friction between the helical spring 448 and the back face of the docking cap 442 is not sufficient to transfer the radial torque required to rotate the docking cap 442 and the leadless capsule, the helical spring 448 slides around the docking shaft 444 until the distal end of the helical spring 448 snags the projection finger 446. The projection finger 446 locks the docking cap 442 in rotation with the helical spring 448 and the torque shaft 452 such that maximum torque is transmitted to the leadless capsule in the direction to unscrew the capsule (see FIGS. 5A-5D for a more detailed description of this interaction).

Figure 5A:
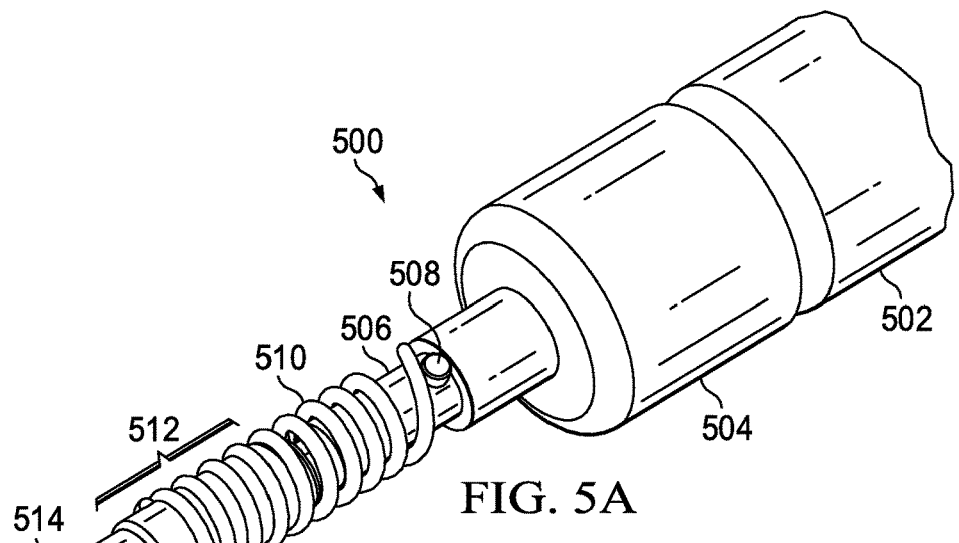
FIG. 5A is a particular illustrative embodiment showing the leadless capsule delivery system with a docking feature and a projection finger.

Referring to FIG. 5A, a particular illustrative embodiment of a delivery system (also referred to as an implantation accessory) is disclosed and generally designated 500. The delivery system 500 delivers a leadless capsule 502 to an implantation site, and includes a docking feature 504, the docking feature including a docking shaft 506 and a projection finger 508 located near the distal end of the docking shaft 506. The docking feature 504 may be secured in translation with the torque shaft 514. The distal end of a helical spring 510 interacts with a back face of the docking feature 504 and the projection finger 508. The helical spring 510 may be coupled to a distal end of a torque shaft 514 via a permanent coupling 512, such as a weld or glue.

The helical spring 510 may be axially pre-compressed between the permanent coupling 510 on distal end of the torque shaft 514 and back face of the docking feature 504 at the distal end of the docking shaft 506. The axial compression creates friction between the distal end of the helical spring 510 and the back face of the docking shaft 506. The friction is such that the helical spring 510 will slide around the docking shaft 506 of the docking feature 504 when radial torque above a limit is applied to the torque shaft 514 (e.g., when the distal face of the leadless capsule 502 contacts the tissue wall).

Figure 5B:
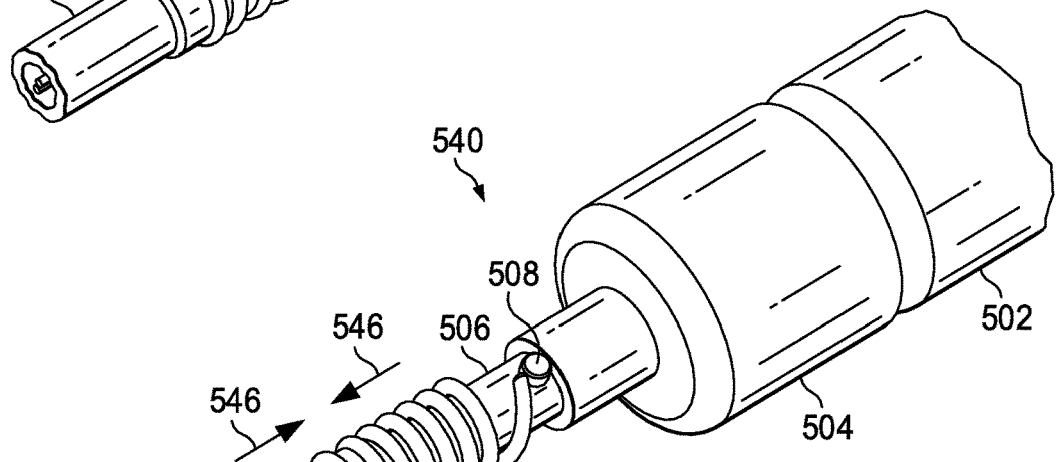
FIG. 5B is a particular illustrative embodiment showing the leadless capsule delivery system with a docking feature and a projection finger with radial torque applied in a first direction.

Referring to FIG. 5B, a particular illustrative embodiment of a delivery system (also referred to as an implantation accessory) is disclosed and generally designated 540. The delivery system 540 illustrates the delivery system 500 under the effects of radial torque applied to the torque shaft 514 in a first radial direction 544, which is the direction to screw the leadless capsule 502 into a tissue wall. Referring also to FIG. 5D, graph 520 graphically illustrates delivery system 500 under the effects of radial torque applied to the torque shaft 514 in the first radial direction 544, where a y-axis 522 represents torque and an x-axis 524 represents the number or turns in a radial direction. The radial torque transmitted from the torques shaft 514 to the leadless capsule 502 is illustrated by line 526. The helical spring 542 transmits a radial torque that is sufficient to screw the leadless capsule 542 into a tissue wall. When the leadless capsule 502 is fully anchored and the distal face of the leadless capsule 502 contacts the tissue wall, the radial torque required to rotate the leadless capsule 502 increases to a radial torque value 534 (e.g., radial torque value T1). However, when the radial torque required to rotate the leadless capsule 502 in the first radial direction 544 exceeds a radial torque value 528 (e.g., radial torque value T3), the helical spring 542 begins to slide around the docking shaft 506 and the torque transmitted does not increase (until the projection finger 508 is engaged by the helical spring 542).

As the helical spring 542 slides around the docking shaft 506, the distal end of the helical spring 542 engages the projection finger 508. This engagement causes the already pre-compressed helical spring 542 to compress further as indicated by arrows 546. The increase in the compressive force increases the friction between the distal end of the helical spring 542 and the docking feature 504, and the torque transmitted to the leadless capsule increases to a radial torque value 530 (e.g., radial torque value T2), but does not reach the radial torque value 534 (e.g. radial torque value T1) required to rotate the fully implanted leadless capsule 502. Therefore, the distal end of the helical spring 542 slides over and passes the projection finger 508 as the helical spring 542 slides around the docking shaft 506. As illustrated by line 526, with each full turn in the first radial direction after the leadless capsule 502 is fully anchored, the distal end of the helical spring 542 engages the projection finger 508 and the torque transmitted to the leadless capsule 502 increases from the radial torque value 528 to the radial torque value 530, but never reaches the radial torque value 534.

As mentioned, the radial torque value 534 is the radial torque value required to continue to rotate the leadless capsule 502 after it is fully anchored to the tissue wall and the distal face of the leadless capsule 502 is in contact with the tissue wall. Continued rotation of the leadless capsule 502 after it has been fully anchored may cause the damage to the tissue, such as coring, and could even puncture the tissue wall. If the tissue wall is a heart wall, the puncture could be life threatening. As illustrated in graph 520, the radial torque transmitted to the leadless capsule never reaches the radial torque value 534 regardless of how many times the operator rotates the torque shaft 514. Hence, the delivery system 500 protects the tissue wall from damage during implantation of the leadless capsule 502.

Figure 5C:
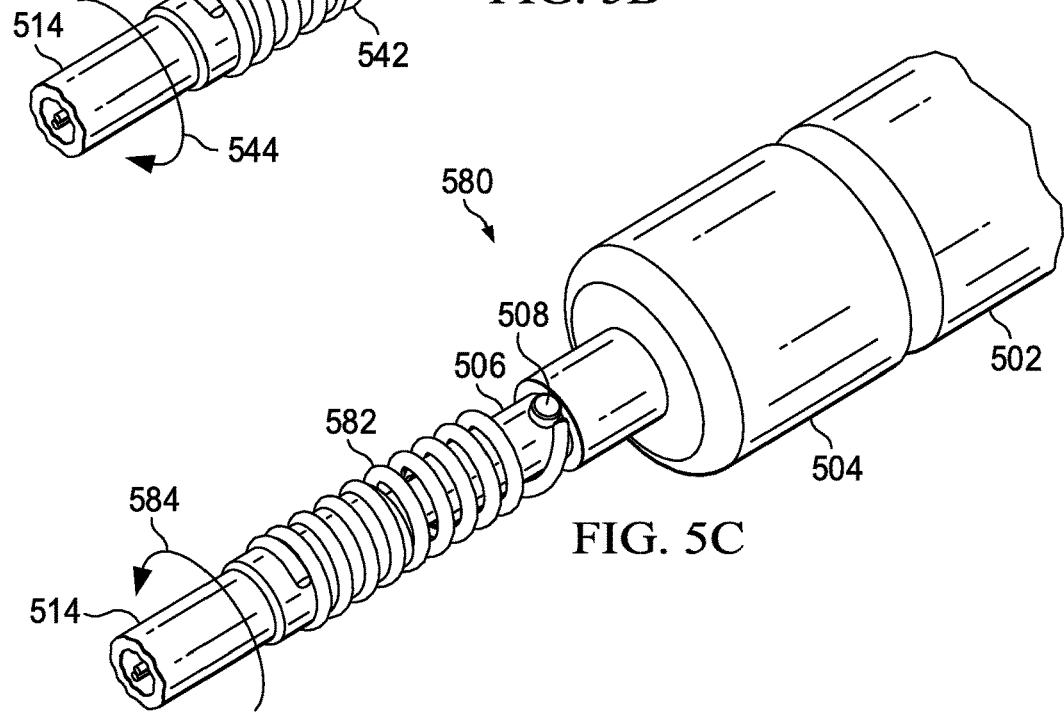
FIG. 5C is a particular illustrative embodiment showing the leadless capsule delivery system with a docking feature and a projection finger with radial torque applied in a second direction.
Figure 5D:
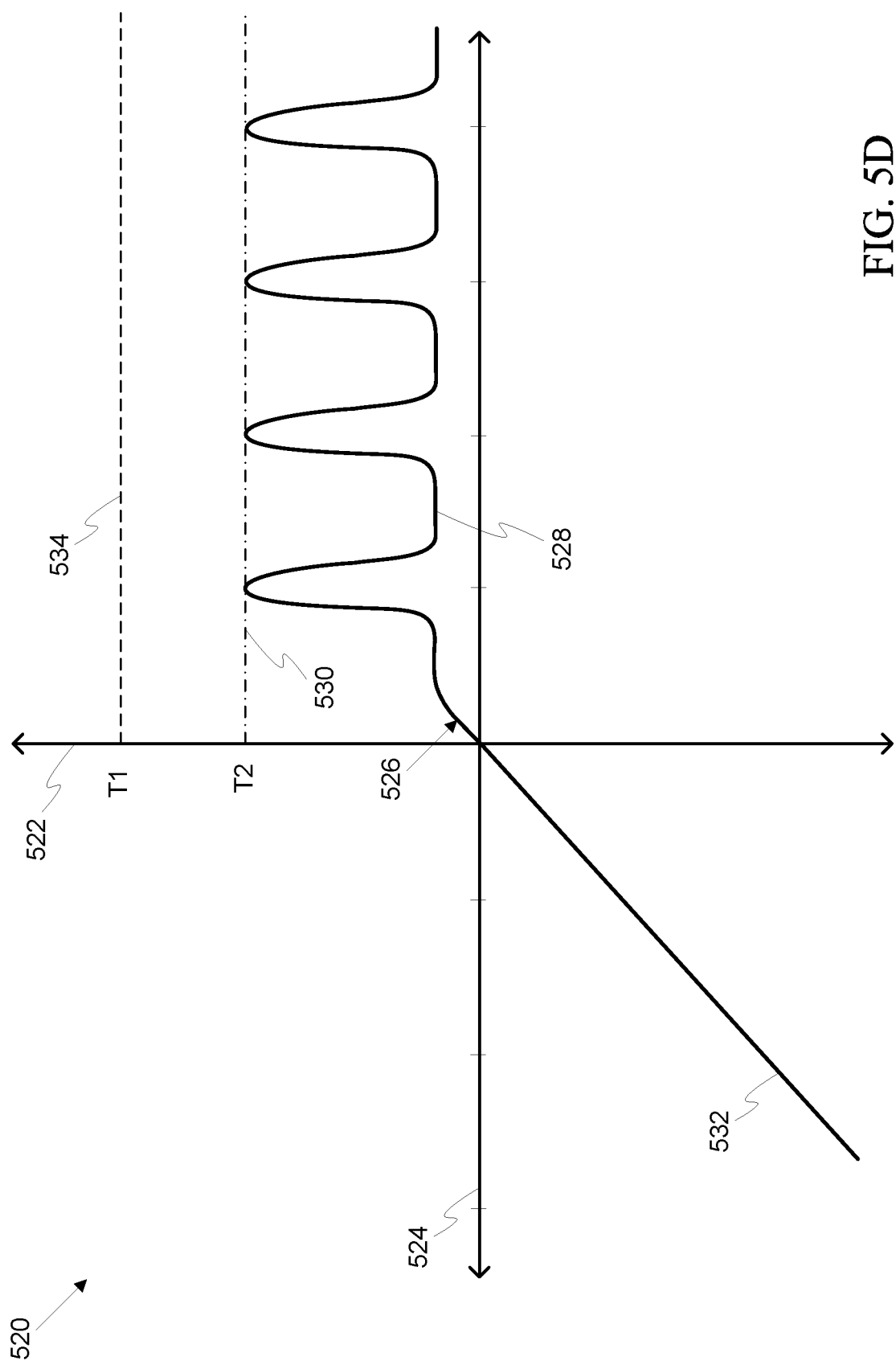
FIG. 5D is a graph illustrating the radial torque transmitted in a leadless capsule delivery system with a docking feature and a projection finger.

Referring to FIG. 5C, a particular illustrative embodiment of a delivery system (also referred to as an implantation accessory) is disclosed and generally designated 580. The delivery system 580 illustrates the delivery system 500 under the effects radial torque applied to the torque shaft 514 in a second radial direction 584, which is the direction to unscrew the leadless capsule 502 from a tissue wall. Referring also to FIG. 5D, graph 520 graphically illustrates delivery system 500 under the effects of radial torque applied to the torque shaft 514 in the second radial direction 584. When the helical spring 582 is rotated by the torque shaft 514 in the second direction, radial torque is transmitted to the docking feature 504. If the friction between the distal end of the helical spring 582 and the back face of the docking feature 504 is not sufficient to transfer the radial torque required to rotate the docking cap 504 and the leadless capsule 502, then the helical spring 582 slides around the docking shaft 506 until the distal end of the helical spring 582 snags the projection finger 508. The projection finger 508 locks the docking cap 504 in rotation with the helical spring 582 and the torque shaft 514 such that maximum torque is transmitted to the leadless capsule 502 in the direction to unscrew the capsule. Line segment 532 of line 526 represents the radial torque transmitted to the leadless capsule 502 in the second radial direction 584 when the distal end of the helical spring 582 snags the projection finger 508. Maximum radial torque is transmitted in the second radial direction 584 and may be sufficient to unscrew the leadless capsule 502 from the tissue wall.

Figure 6A:
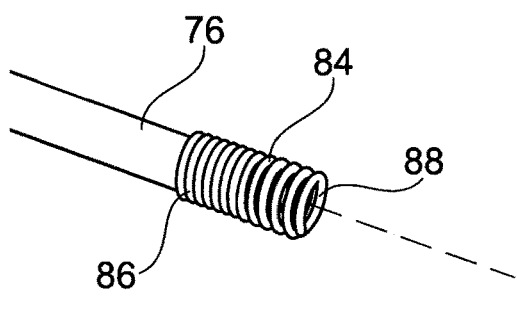
FIG. 6A separately shows the radial compression coil spring mounted on the end of the sub-catheter.
Figure 6B:
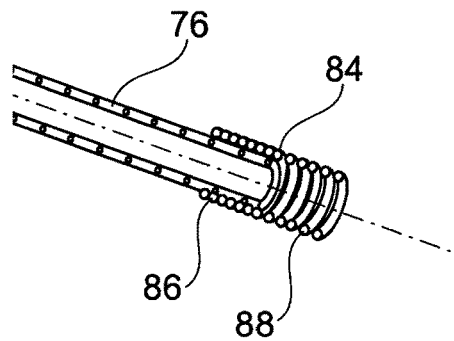
FIG. 6B is a sectional view corresponding to FIG. 6A.

The spring 84, also shown in FIGS. 6A and 6B, may be secured to the distal end of the sub-catheter 76 by turns 86. The turns 86 may be secured by welding, gluing, or some other manner of permanently securing the turns 88 to the sub-catheter 76.

The turns 88 at the distal end of the spring 84 are free turns, which surround the lashing rod 20, or shaft, but which are not mechanically fastened to the latter by connection mechanisms other than an interference fit with tightening obtained in the static configuration of these two elements. In addition, the distal end of the spring 84 may have a rounded end to prevent tissue injury and snagging at various manipulations. The turns 86 and/or the active turns 88 may be either touching or not contiguous.

Once the capsule 10 is affixed to the implantation site after complete penetration of the anchoring screw 14 all the way up to the front face of the capsule, the practitioner, who has limited visibility on the progress of the anchoring, may continue to make the sub-catheter 76 turn, thereby generating an excess torque. The excess torque has the effect of reducing the force exerted by the free turns 88 on the lashing rod 20 and to cause rotational sliding of these turns on the lashing rod 20. The compression spring 84 may be released from the lashing rod 20 by combining the rotational movement and a slight tensile load to cause longitudinal sliding of the turns on the rod until the capsule 10 is released from the spring 84, and thus from the sub-catheter 76.

Figure 6C:
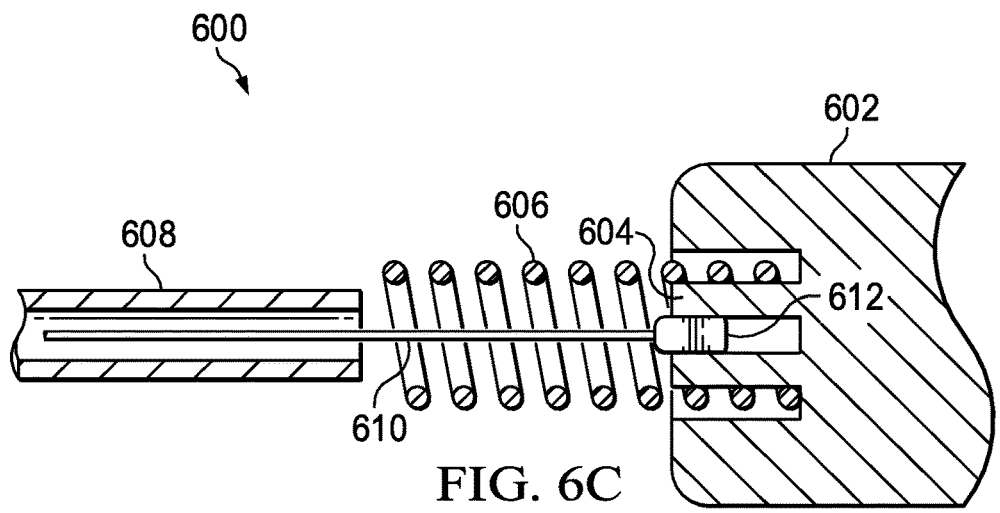
FIG. 6C is a sectional view of a particular illustrative embodiment showing an alternative torque limiter configuration.

Referring to FIG. 6C, a particular illustrative embodiment of a delivery system (also referred to as an implantation accessory) is disclosed and generally designated 600. The delivery system 600 delivers a leadless capsule 602 to an implantation site. The leadless capsule may include capsule shaft 604 (also referred to as a lashing rod) and may be coupled to a helical spring 606 via a permanent coupling, such as a weld or glue. The capsule shaft 604 may be hollow and receive a distal end 612 of a security thread 610. The distal end 612 of the security thread 610 and the hollow portion of the capsule shaft 604 may include corresponding threads to secure the leadless capsule 602 to the security thread 610. The delivery system 600 further includes a sub-catheter 608 (may also be referred to as a torque shaft) that fits inside the helical spring 606 and couples to the helical spring via an interference fit.

With the leadless capsule 602 coupled to the sub-catheter 608, the delivery system 600 may be used to maneuver the leadless capsule 602 to the implantation site. At the implantation site, the anchoring screw at the distal end of the leadless capsule 602 is brought into contact with a tissue wall and a radial torque in a first radial direction (e.g., the direction to screw the leadless capsule 602 into a tissue wall at the implantation site) is applied at the proximal end of the sub-catheter 608. The entire sub-catheter 608 rotates in the first radial direction and delivers a radial torque to the helical spring 606 affixed at the capsule shaft 604 causing the leadless capsule 602 to rotate. The rotation of the leadless capsule 602 drives the anchoring screw into the tissue wall at the implantation site. The torque transferred by the helical spring 606 is sufficient to rotate the leadless capsule 602 until the helical screw is driven into the tissue wall far enough so that the distal face of the leadless capsule 602 comes into contact with the tissue wall. The radial torque required to continue to rotate the leadless capsule 602 increases to a value T1. The continued rotation of the leadless capsule 602 could tear the tissue and potentially puncture the tissue wall. If the tissue wall is a heart wall, the puncture could cause cardiac tamponade.

The helical spring 606, provides a limit to the radial torque that may be transferred to the leadless capsule 602. The limit is a value lower than the radial torque value T1 required to continue rotation of the leadless capsule 602. For example, as the radial torque required to rotate the leadless capsule 602 increases, the friction between the helical spring 606 and the outer surface of the sub-catheter 608 that forms the interference fit is no longer sufficient to secure the helical spring 606 and the sub-catheter 608 in rotation. The helical spring 606 begins to slide around the sub-catheter 608 thereby limiting the radial torque transferred to the leadless capsule 602. Therefore, when the distal face of the leadless capsule 602 contacts the tissue wall, the sub-catheter 608 may continue to rotate in the first direction, but the leadless capsule 602 will no longer rotate and cause tearing of the tissue at the implantation site.

Figure 6D:
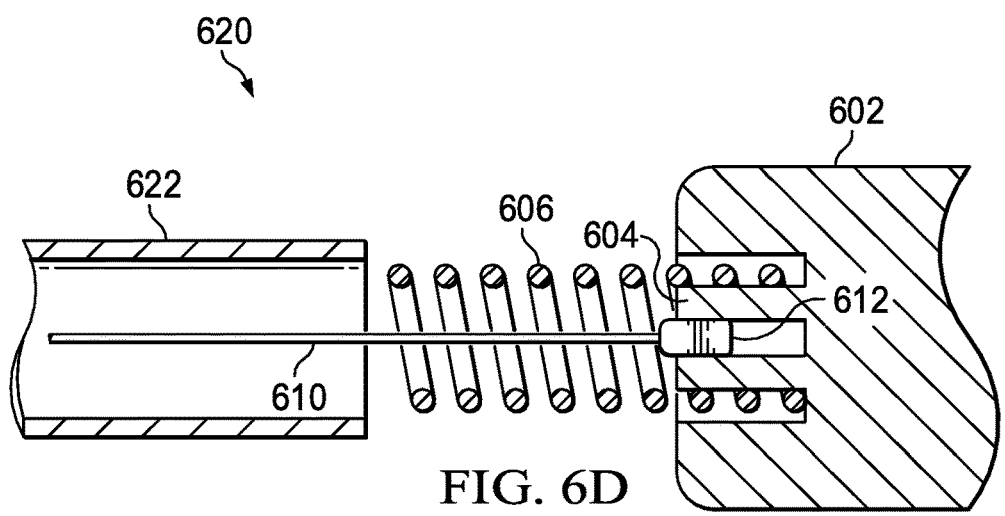
FIG. 6D is a sectional view of another particular illustrative embodiment showing an alternative torque limiter configuration.

Referring to FIG. 6D, a particular illustrative embodiment of a delivery system (also referred to as an implantation accessory) is disclosed and generally designated 620. The delivery system 620 delivers a leadless capsule 602 to an implantation site. The leadless capsule 602 may include a capsule shaft 604 (also referred to as a lashing rod) and may be coupled to a helical spring 606 via a permanent coupling, such as a weld or glue. The capsule shaft 604 may be hollow and receive a distal end 612 of a security thread 610. The distal end 612 of the security thread 610 and the hollow portion of the capsule shaft 604 may include corresponding threads to secure the leadless capsule 602 to the security thread 610. The delivery system 600 further includes a sub-catheter 622 (may also be referred to as a torque shaft) that fits over the helical spring 606 and couples to the helical spring via an interference fit. The inner diameter of the sub-catheter 622 and the helical spring 606 may be sized so that an inner surface of the sub-catheter 622 slightly compresses the turns of the helical spring causing a reactive radial expansion force from the helical spring 606. These opposing forces create the interference or friction fit.

With the leadless capsule 602 coupled to the sub-catheter 622, the delivery system 620 may be used to maneuver the leadless capsule 602 to the implantation site. At the implantation site, the anchoring screw at the distal end of the leadless capsule 602 is brought into contact with a tissue wall and a radial torque in a first radial direction (e.g., the direction to screw the leadless capsule 602 into a tissue wall at the implantation site) is applied at the proximal end of the sub-catheter 622. The entire sub-catheter 622 rotates in the first radial direction and delivers a radial torque to the helical spring 606 affixed at the capsule shaft 604 causing the leadless capsule 602 to rotate. The rotation of the leadless capsule 602 drives the anchoring screw into the tissue wall at the implantation site. The torque transferred by the helical spring 606 is sufficient to rotate the leadless capsule 602 until the helical screw is driven into the tissue wall far enough so that the distal face of the leadless capsule 602 comes into contact with the tissue wall. The radial torque required to continue to rotate the leadless capsule 602 increases to a value T1. The continued rotation of the leadless capsule 602 could tear the tissue and potentially puncture the tissue wall. If the tissue wall is a heart wall, the puncture could cause cardiac tamponade.

The helical spring 606, provides a limit to the radial torque that may be transferred to the leadless capsule 602. The limit is a value lower than the radial torque value T1 required to continue rotation of the leadless capsule 602. For example, as the radial torque required to rotate the leadless capsule 602 in the first radial direction increases, the friction between the helical spring 606 and the inner surface of the sub-catheter 622 that forms the interference fit is no longer sufficient to secure the helical spring 606 and the sub-catheter 622 in rotation. The helical spring 606 begins to slide around the sub-catheter 622 thereby limiting the radial torque transferred to the leadless capsule 602. Therefore, when the distal face of the leadless capsule 602 contacts the tissue wall, the sub-catheter 622 may continue to rotate in the first direction, but the leadless capsule 602 will no longer rotate and cause tearing of the tissue at the implantation site. When the sub-catheter 622 is rotated in the first radial direction, the spring compresses within the sub-catheter 622 thereby reducing the friction between the outer surface of the turns of the helical spring 606 and the inner surface of the sub-catheter 622. This compression limits the torque that is transferred from the sub-catheter 622 to the leadless capsule 602. When the sub-catheter 622 is rotated in a second radial direction (e.g., the direction to unscrew the leadless capsule from the tissue), the helical spring exerts a radial expansion force on the inner surface of the inside of the sub-catheter 622 and increases the friction between the inner surface of the inside of the sub-catheter 622 and the outer surface of the turns of the helical spring 606 to provide maximum torque to the leadless capsule 602.

The foregoing figures and descriptions are illustrative and should not be considered limiting. Various other configurations of the helical spring, sub-catheter, and the coupling mechanism at the proximal end of the capsule (e.g., a capsule shaft) are possible and within the scope of the disclosure.

Figure 7A:
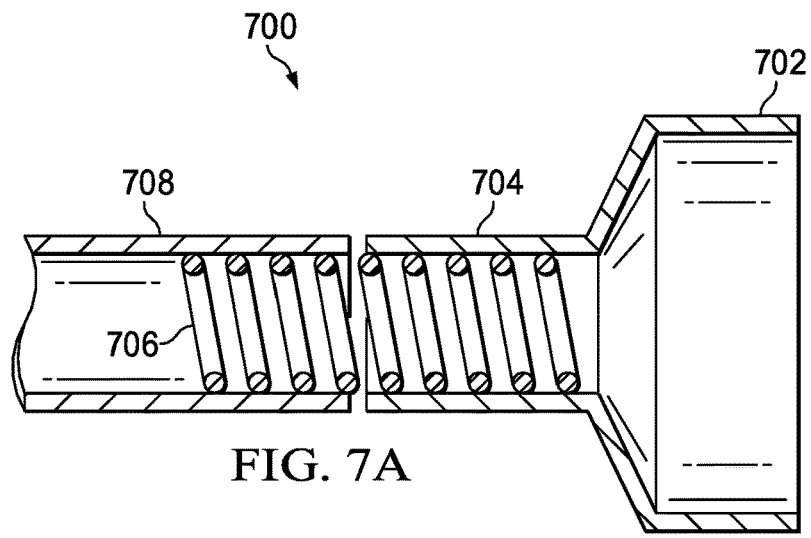
FIG. 7A is a sectional view of a particular illustrative embodiment showing an alternative torque limiter configuration with a docking feature.

Referring to FIG. 7A, a particular illustrative embodiment of a delivery system (also referred to as an implantation accessory) is disclosed and generally designated 700. The delivery system 700 includes a docking feature 702 (e.g., a docking cap) having a docking shaft 704, a torque shaft 708 and a torque limiter, which may be a helical spring 706. The docking feature 702 may be secured in translation with the torque shaft 708. Both the torque shaft 708 and the docking shaft 704 may be hollow. The helical spring 706 is coupled to the distal end of the torque shaft 708 and the proximal end of the docking shaft 704. The proximal portion of the helical spring 706 may fit inside the hollow part of the distal end of the torque shaft 708 and may be permanently coupled to the torque shaft 708 or coupled via and interference fit. The distal end of the helical spring 706 may fit inside the hollow part of the docking shaft 704 and may form an interference fit with the docking shaft 704 or be permanently coupled to the docking shaft 704.

In some embodiments, the permanent coupling is between the outer surface of the helical spring 706 and the inner surface of the docking shaft 704 and the interference fit is between the outer surface of the helical spring 706 and the inner surface of the torque shaft 708. The inner diameter of the torque shaft 708 and the helical spring 706 may be sized so that an inner surface of the torque shaft 708 slightly compresses the turns of the helical spring 706 causing a reactive radial expansion force from the helical spring 706. These opposing forces create the interference or friction fit that limit the torque transmitted from the torque shaft 708 to the docking feature 702 and the corresponding leadless capsule in a first radial direction (e.g., to screw the leadless capsule into a tissue wall) and provide maximum torque in a second radial direction (e.g., to unscrew the leadless capsule from the tissue wall) as describe repeatedly in this disclosure.

In some embodiments, the permanent coupling is between the outer surface of the helical spring 706 and the inner surface of the torque shaft 708 and the interference fit is between the outer surface of the helical spring 706 and the inner surface of the docking shaft 704. The inner diameter of the docking shaft 704 and the helical spring 706 may be sized so that an inner surface of the docking shaft 704 slightly compresses the turns of the helical spring 706 causing a reactive radial expansion force from the helical spring 706. These opposing forces create the interference or friction fit that limit the torque transmitted from the torque shaft 708 to the docking feature 702 and the corresponding leadless capsule in a first radial direction (e.g., to screw the leadless capsule into a tissue wall) and provide maximum torque in a second radial direction (e.g., to unscrew the leadless capsule from the tissue wall) as describe repeatedly in this disclosure.

In some embodiments, the proximal end of the helical spring 706 fits over the torque shaft 708 and the distal end of the helical spring 706 fits inside of the hollow part of the docking shaft 708. In some embodiments, the distal end of the helical spring 706 fits over the docking shaft 708 and the proximal end of the helical spring 706 fits inside the torque shaft 708.

Figure 7B:
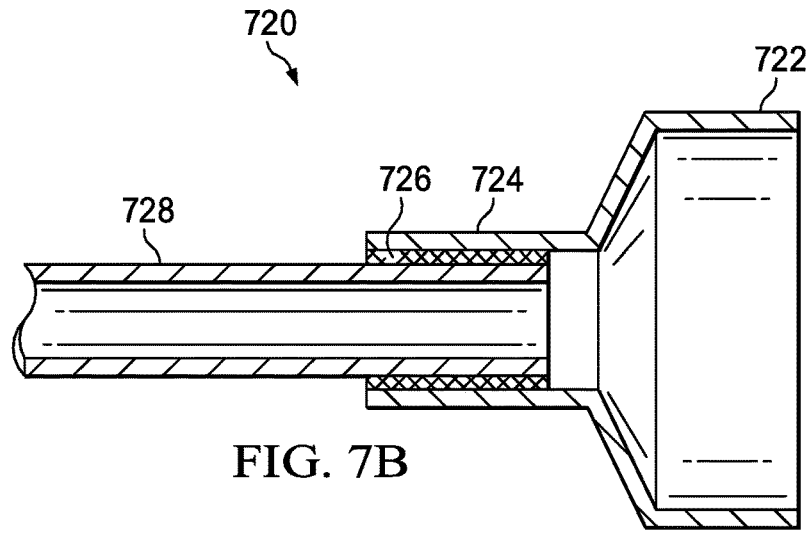
FIG. 7B is a sectional view of another particular illustrative embodiment showing an alternative torque limiter configuration with a docking feature.

Referring to FIG. 7B, a particular illustrative embodiment of a delivery system (also referred to as an implantation accessory) is disclosed and generally designated 720. The delivery system 720 includes a docking feature 722 (e.g., a docking cap) having a docking shaft 724. The docking feature 722 receives the proximal end of the leadless capsule. The docking shaft 724 may be a hollow shaft with an inner diameter for receiving a distal end of a torque shaft 728. The docking feature 722 may be secured in translation with the torque shaft 728. The delivery system 720 also includes a torque limiter 726 disposed between the inner surface of the docking shaft 724 and the outer surface of the distal end of the torque shaft 728. The torque limiter may be in the form of one or more layers of material. The material layer may be affixed to the outer surface of the distal end of the torque shaft 728, affixed to the inner surface of the docking shaft 724, and/or coupled to both the torque shaft 728 and the docking shaft 724 via an interference fit. The material may be a fabric, a coating, or a cylindrical sleeve. The material and dimensions of the layer may be selected to provide a degree of friction such that radial torque may be transmitted from the distal end of the torque shaft 728 to the docking feature 722, and thus, the leadless capsule to screw the leadless capsule into the tissue wall. However, once the distal face of the leadless capsule contacts the tissue wall, the friction between the torque shaft 728 and the docking shaft 724 provided by the material is not sufficient to transmit the radial torque required to rotate the leadless capsule. Therefore, the torque shaft 728 will continue to rotate and slide within the docking shaft 724 without turning the docking feature 722. Thus, the transmitted torque is limited in part by the friction provided by the material disposed between the torque shaft 728 and the docking shaft 724.

Figure 7C:
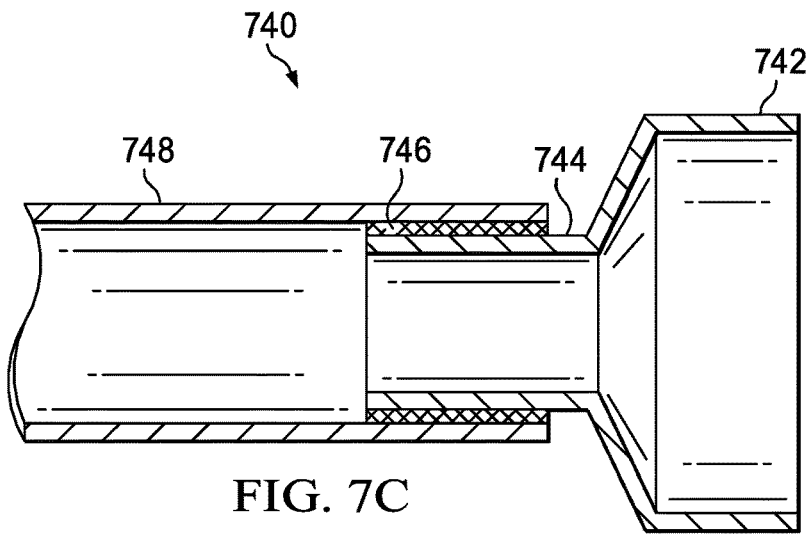
FIG. 7C is a sectional view of another particular illustrative embodiment showing an alternative torque limiter configuration with a docking feature.

Referring to FIG. 7C, a particular illustrative embodiment of a delivery system (also referred to as an implantation accessory) is disclosed and generally designated 740. The delivery system 740 includes a docking feature 742 (e.g., a docking cap) having a docking shaft 744 and a torque shaft 748. The docking feature 742 receives the proximal end of the leadless capsule. The docking feature 742 may be secured in translation with the torque shaft 748. The torque shaft 748 may be a hollow shaft with an inner diameter for receiving a proximal end of the docking shaft 744. The delivery system 740 also includes a torque limiter 746 disposed between the inner surface of the distal end of the torque shaft 748 and the outer surface of the docking shaft 744. The torque limiter may be one or more layers of material. The material layer may be affixed to the inner surface of the distal end of the torque shaft 748, affixed to the outer surface of the docking shaft 744, and/or coupled to both the torque shaft 748 and the docking shaft 744 via an interference fit. The material may be a fabric, a coating, or a cylindrical sleeve. The material and dimensions of the layer may be selected to provide a degree of friction such that radial torque may be transmitted from the distal end of the torque shaft 748 to the docking feature 742, and thus, the leadless capsule to screw the leadless capsule into the tissue wall. However, once the distal face of the leadless capsule contacts the tissue wall, the friction between the torque shaft 748 and the docking shaft 744 provided by the material is not sufficient to transmit the radial torque required to rotate the leadless capsule. Therefore, the torque shaft 748 will continue to rotate and slide around the docking shaft 744 without turning the docking feature 742. Thus, the transmitted torque is limited in part by the friction provided by the material disposed between the torque shaft 748 and the docking shaft 744.

Figure 8A:
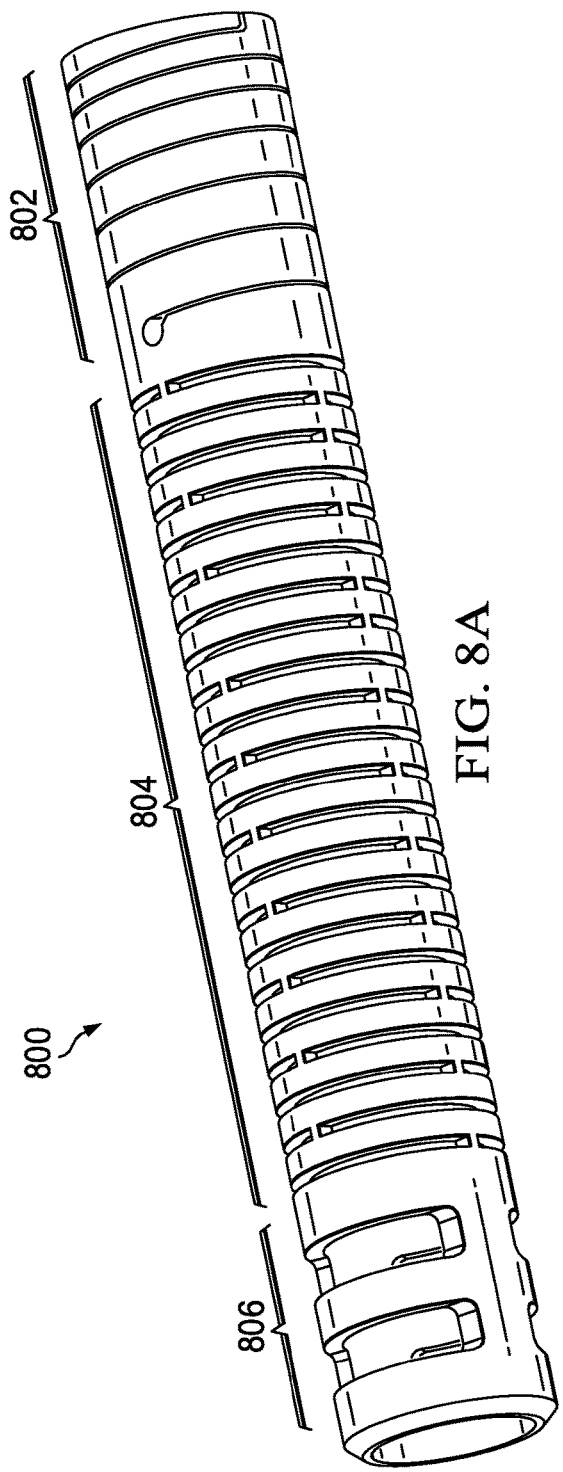
FIG. 8A is a particular illustrative embodiment showing laser etched component for a torque limiter.

Referring to FIG. 8A, a particular illustrative embodiment of a torque limiter is disclosed and generally designated 800. The torque limiter 800 includes a first end portion 802, and middle portion 804 and a second end portion 806. The first end portion 802 may be a distal end and may couple to either a docking shaft of a docking feature or a capsule shaft of a leadless capsule. In some embodiments, the first end portion 802 may be a proximal end and may couple to a torque shaft (or a sub-catheter). The first end portion 802 may provide an interference fit with the corresponding component to which it couples. The first end portion 802 may be a helical spring with turns that provide a radial compression around a rigid component such as a torque shaft, a docking shaft, or a capsule shaft, and may function in a similar manner to the helical springs 84, 424, 606, and 706 already described.

The middle portion 804 is an optional flexible portion. The middle portion 804 may be sized according to the particular needs and dimensions of the delivery system to improve or provide the flexibility for implantation of the leadless capsule. The second end 806 includes holes or gaps to facilitate permanent coupling by welding, gluing, or some other attachment mechanism.

The torque limiter 800 may be laser etched, or otherwise cut, from inox or Mp35N metal tubing, or nitinol tubing. Laser etching provides various advantages over a wound wire to form the helical spring. For example, the laser etched torque limiter, including the spring portion (the first end portion 802), may be manufactured with less variation and have a more stable torque limit. Laser etching also allows for certain features to be incorporated into the torque limiter such as a distal chamfer in the inner diameter to more easily receive the rigid coupling component (e.g., the torque shaft, docking shaft, or capsule shaft), and a distal inner protuberance to make the torque limit of the spring less sensitive to its longitudinal position on the rigid component.

Figure 8C:
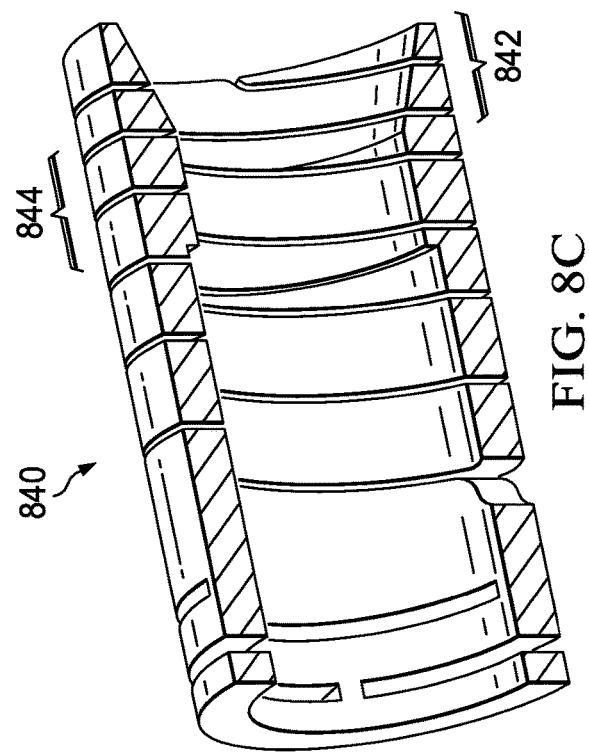
FIG. 8C is a sectional view of alternative embodiment of the laser etched component for a torque limiter.
Figure 8B:
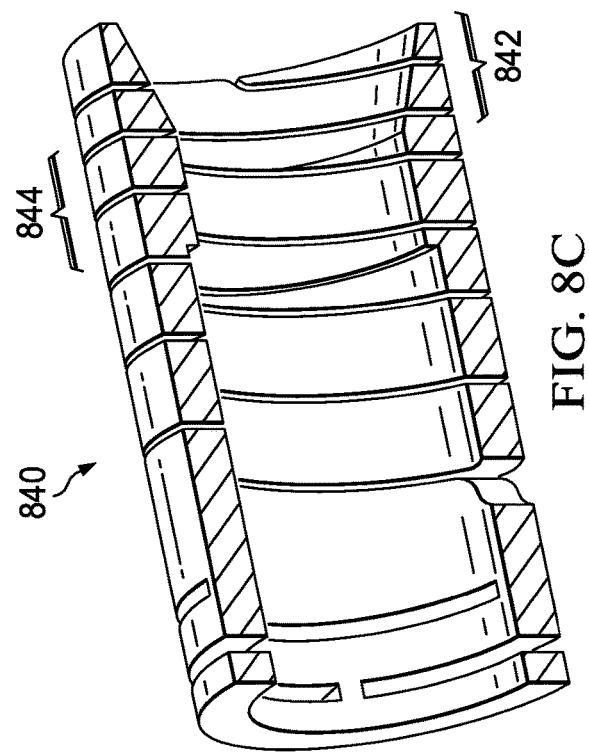
FIG. 8B is a sectional view of the laser etched component of FIG. 8A.
Figure 9A:
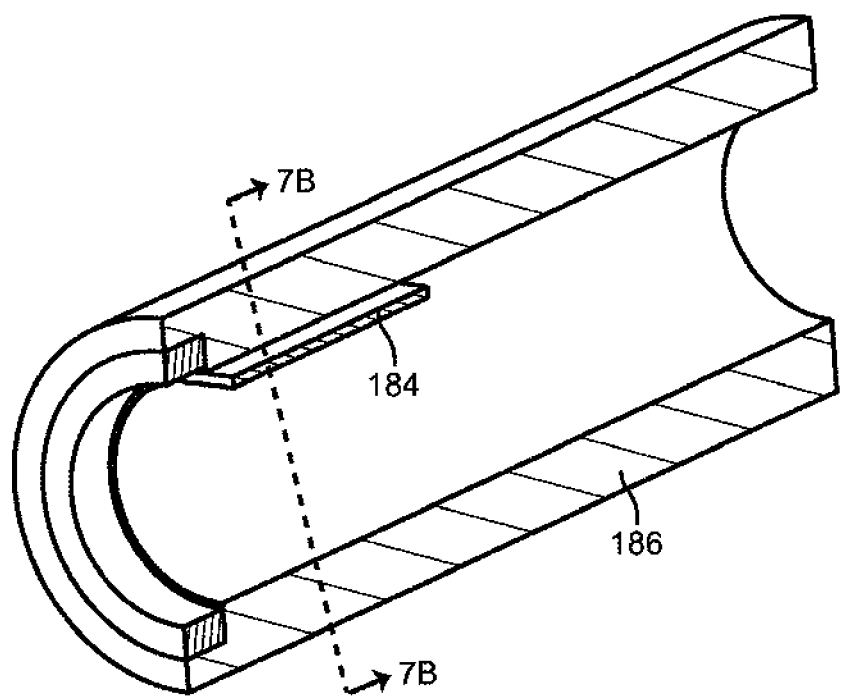
FIG. 9A is a sectional view showing a socket of a hollow cylinder housing a lamella.
Figure 9B:
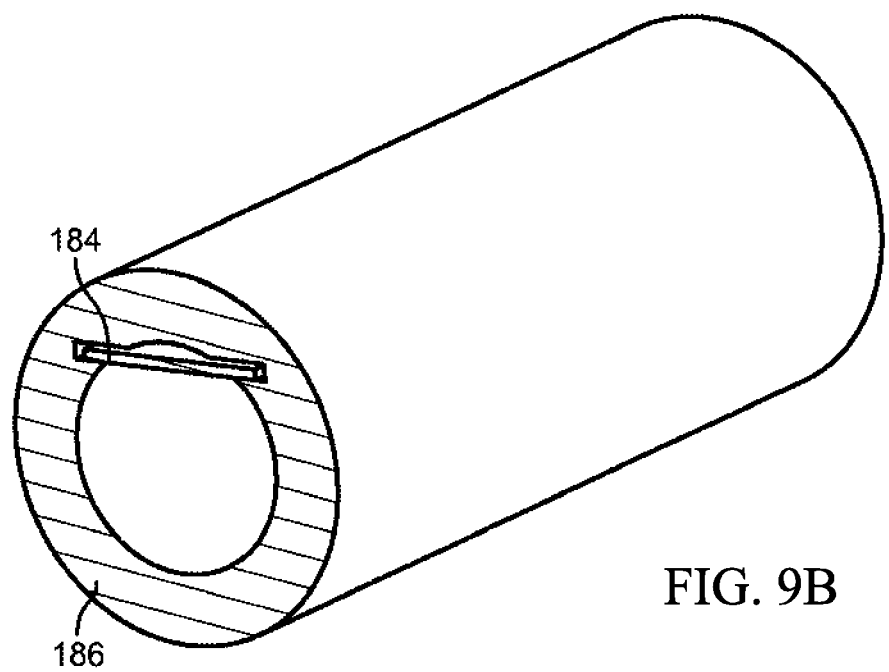
FIG. 9B is a sectional view corresponding to FIG. 9A.
Figure 9C:
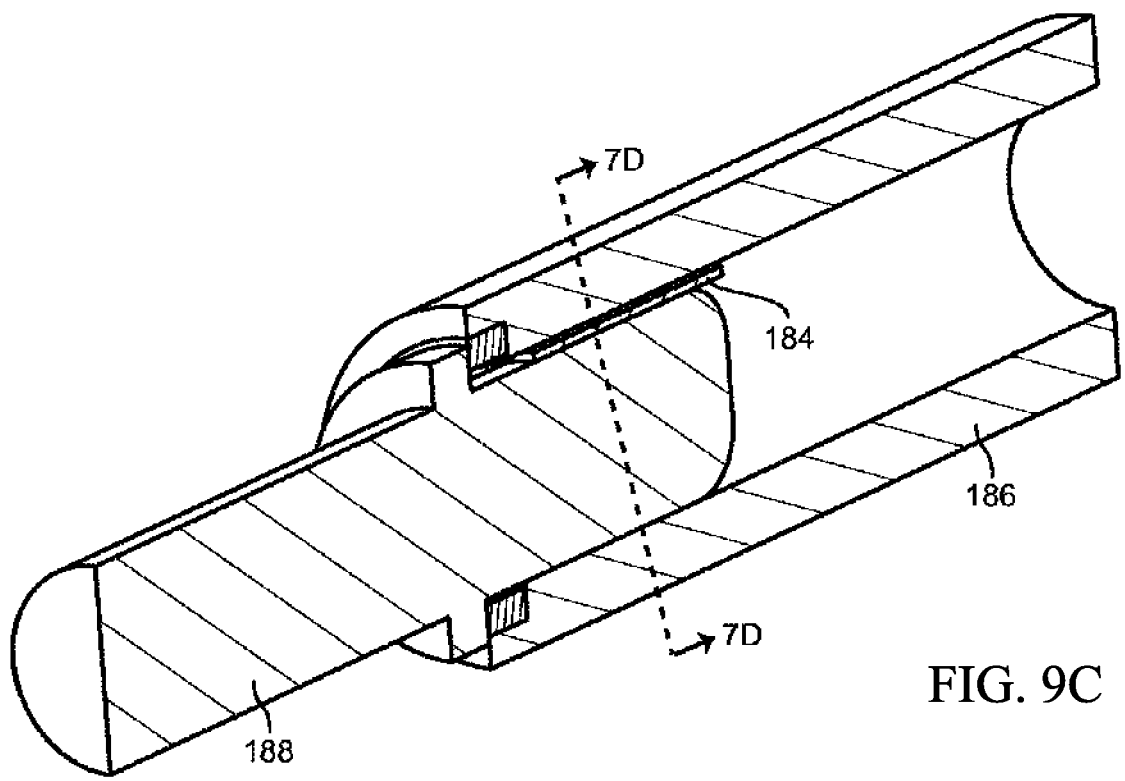
FIG. 9C is a sectional view of a non-deformable axis inserted into the hollow cylinder housing of FIG. 9A.
Figure 9D:
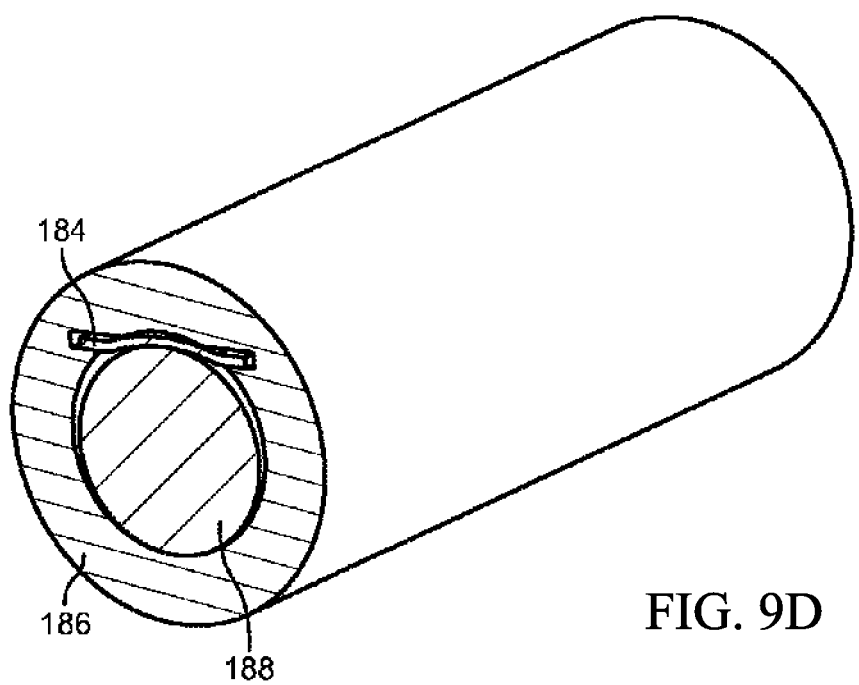
FIG. 9D is a sectional view corresponding to FIG. 9C.

Referring to FIG. 8B, a particular illustrative embodiment of an end portion of a torque limiter is disclosed and generally designated 820. The end portion 820 of the torque limiter may couple to a leadless capsule shaft (e.g., a lashing rod), a docking shaft of a docking feature, or a torque shaft. The end portion 820 may include a distal chamfer 822 or slightly sloped inner surface at the distal end of the end portion 820 to make it easier for the end portion 820 to receive a rigid component such as the capsule shaft, docking shaft, or torque shaft. The end portion 820 slides over the capsule shaft, docking shaft, or torque shaft to form an interference fit.

Referring to FIG. 8C, a particular illustrative embodiment of an end portion of a torque limiter is disclosed and generally designated 840. The end portion 840 may couple to a leadless capsule shaft (e.g., a lashing rod), a docking shaft of a docking feature, or a torque shaft. The end portion 840 may include a distal chamfer 842 or slightly sloped inner surface at the distal end of the end portion 840 to make it easier for the end portion 840 to receive the capsule shaft, docking shaft, or torque shaft. The end portion 840 may also include an inner protuberance 844 at the distal end of the torque limiter. The inner protuberance 844 reduces the surface area in contact with the rigid component to make the torque limit of the spring less sensitive to its position on the rigid component.

In some embodiments, the first end portion 802 of the torque limiter 800 could be designed to fit inside a hollow shaft, such as a hollow docking shaft, capsule shaft, or torque shaft, where the inner surface of the hollow shaft compresses the first end portion 802 and the first end portion 802 provides a reactive expansion force to provide the interference fit or friction fit. The distal chamfer 822 of the end portion 820 could be designed to have a sloped outer surface such that the outer diameter decreases in the distal direction to make it easier for the end portion 820 to fit into the hollow shaft. Also, the inner protuberance 844 could be an outer protuberance and be provided on the outer surface of the distal end of the torque limiter 800.

In an alternative embodiment of the fastening mechanism, shown in FIGS. 9A-9D, the deformable plastic member may be a lamella 184 positioned in a socket created by a hollow cylinder 186. The lamella 184 is radially deformable relative to the cylinder axis. A rigid component is provided in the form of a non-deformable plug element 188 configured to be introduced into the socket of the hollow cylinder 186. The introduction causes deformation of the lamella 184, thereby producing a radial force between the plug element 188 and the lamella 184, as shown in 7D. Relative rotational movement between the hollow cylinder 186 and the plug element 188 generates a tangential calibrated friction and therefore creates a limitation in the torque applied to the components of the system.

The radial compression spring 84 and lamella 184 thus act as a torque limiter. During implantation of the leadless capsule 10, the practitioner might continue rotating the sub-catheter 76, and therefore of the capsule 10, after the capsule is already sufficiently anchored to the heart wall. Without the torque limiter, this continued rotation might increase the torque and exceed a limit, $C_{coring}$, which increases the risk of the anchoring screw locally tearing the tissues and, in the extreme, a perforation of the heart wall, with the risk of tamponade. If the torque limiter is used, the practitioner may safely continue to rotate the sub-catheter 76 in the same direction because the extra torque (the sudden increase of the torque when the front face of the capsule contacts the cardiac tissue) is absorbed by the connection between, for example, the spring 84 and the lashing rod 20. More specifically, the geometry and elasticity of the spring 84 are chosen so as to define a torque $C_{release}$ lower than the coring limit, $C_{coring}$, corresponding to a limit holding torque of the anchoring screw in this tissue, without coring of the tissue, while providing a full screw (tissue contacting the front face of the capsule). Thus, when the $C_{release}$ torque is reached, the further rotation of the sub-catheter 76 in the clockwise direction, in combination with a slight traction force, causes the gradual release of the spring 84 with the lashing rod 20 by longitudinal sliding of the turns of the radial spring along the rod. In case of any excess torque, the turns of the radial spring slide in rotation on the securement ring therefore no longer transmit torque elevation. The clutch release torque $C_{release}$ is adjusted to a typical value of about 0.1 to 0.5 Ncm.

Furthermore, in a static configuration, the pinch force of the free turns 88 of the spring 84 on the lashing rod 20 is selected so as to prevent accidental disassembly by a traction force (axially directed force) lower to a sufficient threshold, typically a threshold which provides holding even for a traction exerted on the sub-catheter 76 under a force of up to 20 N.

Under various circumstances, it may be desirable to unscrew the capsule, for example, to move the capsule to a new site, and to remove the capsule if it is defective or the battery has expired. The coupling system, including the spring 84, will have no release effect during unscrewing. Since the spring will then be driven in reverse rotation (usually counterclockwise), this will further increase the effect of the tightening of the turns 88 on the lashing rod 20.

After the release of the capsule, the implantation accessory or delivery device is present with the free turns 88 of the spring 84, as shown in FIGS. 6A-6B. In case of reoperation intraoperative, that is to say, if it is desirable to secure the new sub-catheter 76 to the capsule, the spring 84 will have the advantage of requiring no angular adjustment to secure the lashing rod 20 of the capsule to be retrieved (unlike the systems using a male/female connector which require positioning to allow the interlocking of the two elements).

Finally, note that the torque limiter the comprising spring 84 is conveniently located in the chain of transmission of forces. Specifically, any loss of fidelity in the transmission of torque between the proximal end of the sub-catheter 76 (e.g., the handle manipulated by the practitioner) and its distal end (the spring 84) has no effect on the maximum or minimum torque at the interface between the anchoring screw and the tissue. This is not the case for a detachable system located further upstream, typically in the operating handle 46.

The capsule may be anchored and then released by a combined screwing and traction movement in two steps. First, screwing of the capsule in the heart wall by clockwise rotation of the sub-catheter 76 (e.g. 10 rpm) under a slight push. Second, release of the capsule by a further clockwise rotation of the sub-catheter 76 (e.g. 5 turns) under slight tension to allow removal of the sub-catheter after release of the spring 84. To obtain this result, the direction of the turns of the spring is selected in the same direction as that of the anchoring screw, for example, with a right-engaging thread, so that the screwing of the capsule and then its release correspond to a rotation of the sub-catheter 76 in the clockwise direction, the most conventional one.

In some embodiments, the implantation accessory or delivery system also includes a security thread or retaining wire 90 connected to the capsule 10 on the distal side and extending over the entire length of the sub-catheter 76 and the operating handle 46.

Figure 13:
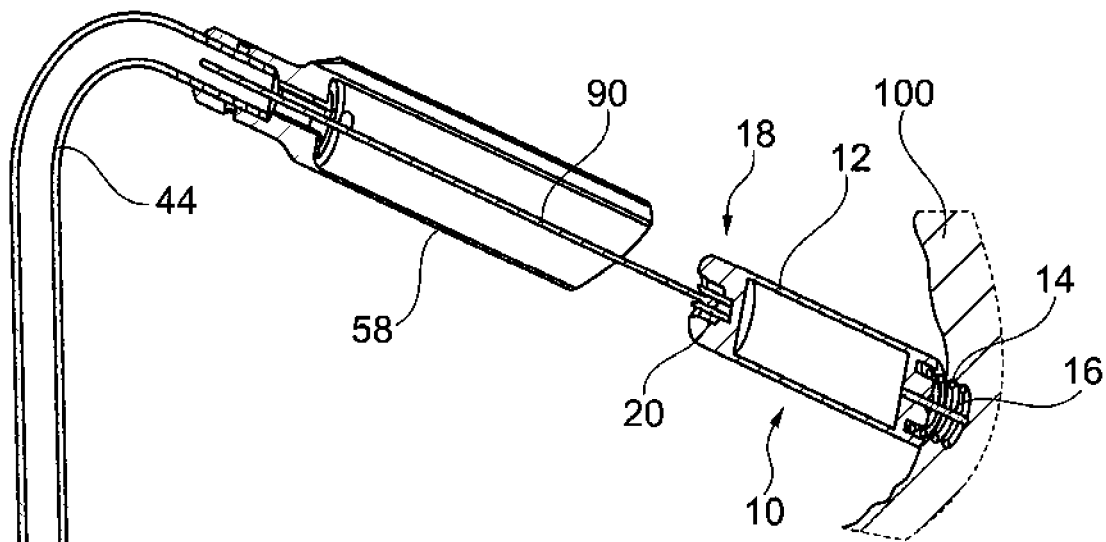
FIG. 13 is an enlarged and sectional homologous view of FIG. 12, once the capsule is implanted in the chosen site, after removal of the sub-catheter and with the retaining wire still in place.
Figure 14:
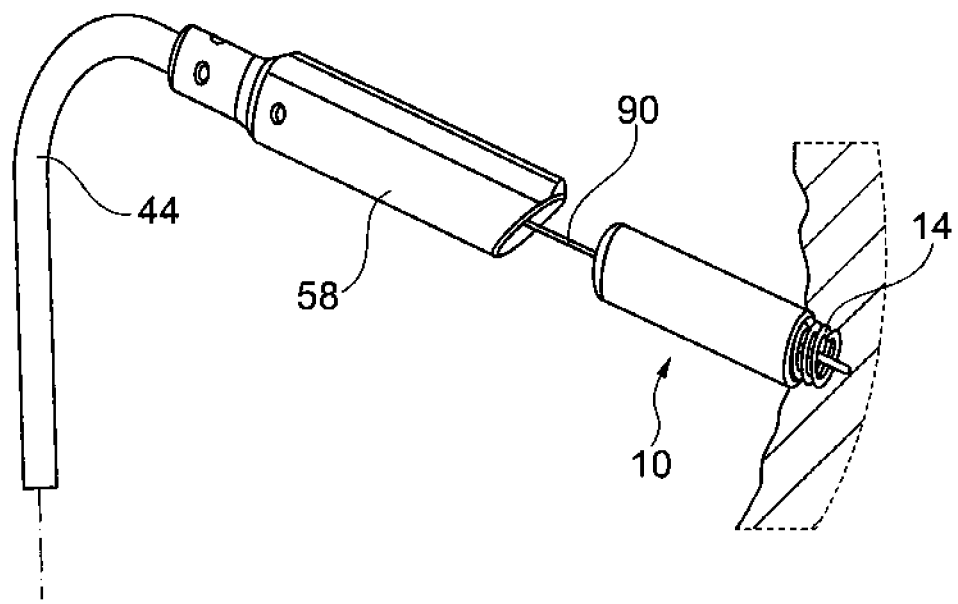
FIG. 14 shows the final configuration of the capsule and the implantation accessory in the situation corresponding to that of FIG. 13.

Referring to FIGS. 13 and 14, once the capsule 10 is implanted and dropped, its operation is tested, including the establishment of good wireless communication between the capsule and the remote master device as well as the stimulation electrical performance.

Once the steerable catheter 44 and the sub-catheter 76 are completely removed, the retaining wire 90 allows for intraoperatively retrieving the capsule, with reintroduction of the implantation accessory by making it slide along the retaining wire 90 until the protection tip 58 caps the capsule 10. The capsule may then be re-coupled to the sub-catheter by a rotation under a slight push (e.g., a clockwise rotation). Once recoupled to the sub-catheter 76, the capsule 10 can then be unscrewed from the wall 100 by a rotation (e.g., a counterclockwise rotation) and repositioned at another site by the same principle as what has been described above.

The retaining wire 90, for example, may be 1 French diameter (0.43 mm) having at its distal end 92 a thread 94 able to cooperate with a mating internal thread 96 formed in a threaded axial bore of the stowage axis 20 (FIG. 3B). The retaining wire 90 may be flexible in its distal part (6 to 8 cm), while being able to transmit to the distal end 92 an unscrewing torque resulting from a rotation exerted from the proximal end, at the operating handle. Due to the very small diameter of the screwing system 94, 96, the torque exerted to unscrew the retaining wire 90 is very small (on the order of 0.02 Ncm), and should not rotate the capsule 10 when secured to the heart wall by the anchoring screw. The retention wire 90 may be colored in different colors for each of the implanted capsules, so as to more easily identify the appropriate capsule in the event of reoperation.

The torque limiter of the delivery system allows from complete fixation of the capsule to the tissue while preventing coring of the heart wall and allows the practitioner to recover the capsule after it is released, through the retaining wire.

Figure 12:
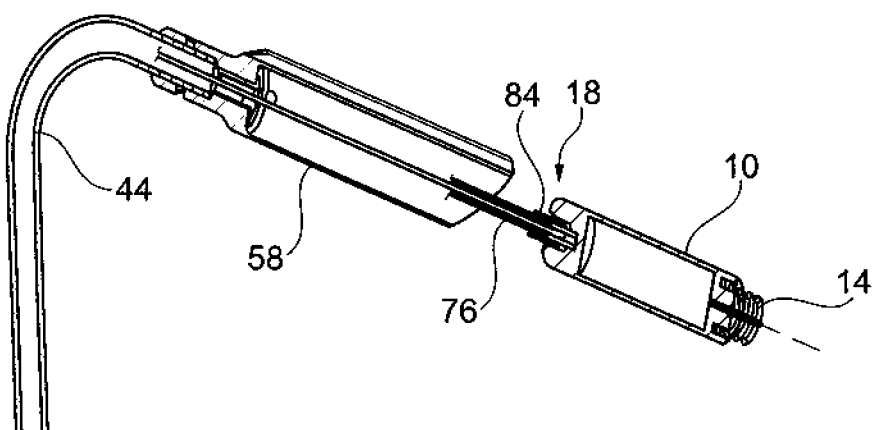
FIG. 12 is an enlarged, sectional view of FIG. 11, showing the general configuration of the different internal elements.

The procedure for implanting the leadless capsule using the implantation accessory described above may include:

Right or left femoral puncture, in order to access the inferior vena cava 30;

Optional percutaneous introduction of a 23 French haemostatic introducer (7.66 mm);

Insertion of the steerable catheter 44 on a spiral guidewire (illustrated at 98 in FIG. 10), typically a 3 French (1 mm) guidewire on which the tubular tip 58, and thus the steerable catheter 44 will slide and move to the right atrium 38;

Turning maneuver of the tip of the steerable catheter 44 (as shown at 36 in FIG. 1A) and introduction of the tip 58 in the right ventricle;

Position the capsule 10 at the apex of the ventricle by translation of the sub-catheter 76 in the steerable catheter 44 (configuration shown in FIG. 12);

Visualization of the cardiac walls by injection of contrast medium through the sub-catheter;

Fine positioning of the capsule to the selected target site, with the possibility of translation once in the cardiac cavity by deployment of the sub-catheter 76 from the steerable catheter 44, allowing fine adjustment to suit a wide variety of anatomies;

Screwing of the capsule in the heart wall to the release of the radial compression spring 84;

Separation of the sub-catheter 76 with the capsule 10, and removing of the sub-catheter 76 out of the steerable catheter 44 (configuration shown in FIG. 13);

Electrical test of the capsule;

Complete removal of steerable catheter 44 and of the sub-catheter 76;

Final release of the capsule, with withdrawal of the retaining wire 90 by low torque unscrewing; and Closure of the puncture site.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. For example, method steps may be performed in a different order than is shown in the figures or one or more method steps may be omitted. Accordingly, the disclosure and the figures are to be regarded as illustrative rather than restrictive.

Moreover, although specific embodiments have been illustrated and described herein, it should be appreciated that any subsequent arrangement designed to achieve the same or similar results may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, the claimed subject matter may be directed to less than all of the features of any of the disclosed embodiments.

What is claimed is:

1. A delivery system for a leadless active implantable medical device, comprising:
   a delivery catheter;
   a torque shaft disposed within the delivery catheter;
   a docking cap having a distal end for engaging an attachment mechanism of the leadless active implantable medical device, a cavity shaped to receive the leadless active implantable medical device including the attachment mechanism, and a projection extending radially outwards from a proximal end of the docking cap; and
   a torque limiting component coupled to a distal end of the torque shaft and the proximal end of the docking cap,
   wherein the torque limiting component is configured to secure the docking cap in translation and rotation until a predetermined torque limit is reached and to interact with the projection of the docking cap when the predetermined torque limit is exceeded;
   wherein when the predetermined torque limit is exceeded, the docking cap remains coupled to the torque limiting component.

2. The delivery system of claim 1, wherein the torque limiting component limits the torque transmission from the torque shaft to the docking cap.

3. The delivery system of claim 1, wherein the torque limiting component limits the torque transmission from the torque shaft to the docking cap to a greater extent when radial torque is applied to the torque shaft in a first radial direction than when radial torque is applied to the torque shaft in a second radial direction.

4. The delivery system of claim 1, wherein the torque limiting component is a helical spring.

5. The delivery system of claim 4, wherein the proximal end of the docking cap is a cylindrical shaft, wherein a proximal end of the helical spring is affixed to the distal end of the torque shaft and a distal end of the helical spring fits over the cylindrical shaft of the docking cap to form an interference fit.

6. The delivery system of claim 4, wherein radial constriction of the helical spring is reduced when radial torque is applied to the torque shaft in a first radial direction.

7. The delivery system of claim 6, wherein the reduction in the radial constriction of the helical spring limits the radial torque transmitted from the torque shaft to the docking cap to a value, wherein the value is less than a radial torque that would cause coring of a tissue at an implantation site.

8. The delivery system of claim 6, wherein radial constriction of the helical spring is increased when radial torque is applied to the torque shaft in a second radial direction.

9. The delivery system of claim 8, wherein the increase in the radial constriction of the helical spring transmits sufficient torque from the torque shaft to the docking cap to safely remove an implanted leadless active implantable medical device from an implantation site.

10. The delivery system of claim 1, wherein the docking cap is configured to decouple from the torque shaft when a tensile load is applied to the torque shaft and when a second predetermined torque limit greater than the predetermined torque limit is exceeded.

\* \* \* \* \*